United States Patent
Geraghty et al.

(10) Patent No.: US 10,112,024 B2
(45) Date of Patent: Oct. 30, 2018

(54) MEDICAL TUBE APPARATUS

(71) Applicant: Monitoring for Life, LLC, Londonderry, NH (US)

(72) Inventors: Scott P. Geraghty, Londonderry, NH (US); Dennis M. Werger, Dunstable, MA (US)

(73) Assignee: Monitoring For Life LLC, Londonderry, NH (US)

( * ) Notice: Subject to any disclaimer, the term of this patent is extended or adjusted under 35 U.S.C. 154(b) by 75 days.

(21) Appl. No.: 15/136,587

(22) Filed: Apr. 22, 2016

(65) Prior Publication Data
US 2016/0296719 A1 Oct. 13, 2016

Related U.S. Application Data

(63) Continuation-in-part of application No. PCT/US2015/011818, filed on Jan. 16, 2015.
(Continued)

(51) Int. Cl.
*A61M 16/04* (2006.01)
*A61M 16/08* (2006.01)
*A61M 16/10* (2006.01)

(52) U.S. Cl.
CPC .... *A61M 16/0486* (2014.02); *A61M 16/0434* (2013.01); *A61M 16/0463* (2013.01);
(Continued)

(58) Field of Classification Search
CPC ............ A61B 1/00052; A61B 1/00087; A61B 1/00124; A61B 1/00135; A61B 1/00154;
(Continued)

(56) References Cited

U.S. PATENT DOCUMENTS 2,797,683 A * 7/1957 Aiken .................. A61B 1/2676
385/902
4,334,534 A * 6/1982 Ozaki .................. A61M 16/04
128/207.15
(Continued)

FOREIGN PATENT DOCUMENTS

WO 2014004762 1/2014

OTHER PUBLICATIONS

International Preliminary Report on Patentability dated Jul. 28, 2016, issued in PCT Patent Application No. PCT/US2015/011818, 7 pages.
(Continued)

*Primary Examiner* — Annette Dixon
(74) *Attorney, Agent, or Firm* — Grossman Tucker Perreault & Pfleger PLLC

(57) ABSTRACT

An endotracheal tube apparatus comprising an endotracheal tube and a hub connection fitting connected with the endotracheal tube. The endotracheal tube is configured to be inserted into a trachea of human body. A ventilation passageway is within the hub connection fitting and along a length of the endotracheal tube. The hub connection fitting may include a power source and a light emitting device. The hub connection fitting may also include a sensor apparatus configured to detect one or more respiration gases of the human body, wherein the sensor apparatus is powered by the power source.

27 Claims, 27 Drawing Sheets

Related U.S. Application Data

(60) Provisional application No. 61/928,685, filed on Jan. 17, 2014, provisional application No. 62/151,899, filed on Apr. 23, 2015, provisional application No. 62/195,577, filed on Jul. 22, 2015.

(52) U.S. Cl.
CPC ...... *A61M 16/0488* (2013.01); *A61M 16/085* (2014.02); *A61M 16/0816* (2013.01); *A61M 16/1065* (2014.02); *A61M 2205/3553* (2013.01); *A61M 2205/3569* (2013.01); *A61M 2205/3592* (2013.01); *A61M 2205/50* (2013.01); *A61M 2205/502* (2013.01); *A61M 2205/7536* (2013.01); *A61M 2205/8206* (2013.01); *A61M 2230/432* (2013.01)

(58) Field of Classification Search
CPC . A61B 1/00165; A61B 1/0017; A61B 1/0051; A61B 1/015; A61B 1/042; A61B 1/05; A61B 1/0676; A61B 1/07; A61B 1/127; A61B 1/267; A61B 1/2676; A61B 1/3132; A61B 17/3415; A61B 17/3417; A61B 2017/3492; A61B 2090/0807; A61B 2090/0811; A61B 2090/306; A61B 2090/373; A61B 5/0075; A61B 5/029; A61B 5/097; A61B 5/0084; A61B 5/0205; A61B 5/0836; A61B 5/1459; A61B 90/361; A61F 9/00736; A61F 9/0079; A61J 15/0003; A61J 15/0007; A61J 15/0026; A61J 15/0049; A61J 15/0073; A61J 15/0092; A61L 2/10; A61L 2202/14; A61L 2202/24; A61M 16/04; A61M 16/042; A61M 16/0422; A61M 16/0425; A61M 16/0434; A61M 16/0438; A61M 16/0459; A61M 16/0463; A61M 16/0486; A61M 16/0488; A61M 16/0493; A61M 16/06; A61M 16/08; A61M 16/0808; A61M 16/0816; A61M 16/085; A61M 16/0858; A61M 16/0875; A61M 16/105; A61M 16/107; A61M 16/16; A61M 2016/0027; A61M 2016/0413; A61M 2205/32; A61M 2205/3306; A61M 2209/10; A61M 2230/205; A61M 2230/432; A61M 2230/435; A61M 25/01; A61M 25/0127; A61N 2005/0604; A61N 2005/0651; A61N 5/0601; Y10S 128/909; Y10S 128/911; Y10S 128/912; Y10S 385/902
USPC ............ 128/200.24, 200.26, 202.27, 205.23, 128/207.14, 207.15, 207.16, 207.17, 911, 128/912; 600/101, 104, 109, 114, 120, 600/139, 156, 160, 184, 194, 199, 249, 600/323, 478, 532; 604/100.01, 164.08, 604/21, 264, 267, 45, 516, 95.01, 96.01, 604/99.01, 99.04; 606/15, 16, 185, 4
See application file for complete search history.

(56) References Cited

U.S. PATENT DOCUMENTS

| | | | |
|---|---|---|---|
| 4,488,548 A * | 12/1984 | Agdanowski | A61M 16/0486 128/204.25 |
| 4,567,882 A * | 2/1986 | Heller | A61M 25/01 128/200.26 |
| 4,669,463 A | 6/1987 | McConnell | |
| 4,834,087 A * | 5/1989 | Coleman | A61M 16/04 128/207.14 |
| 4,850,371 A * | 7/1989 | Broadhurst | A61B 5/0205 128/207.14 |
| 5,193,544 A * | 3/1993 | Jaffe | A61B 5/0836 128/207.14 |
| 5,357,946 A * | 10/1994 | Kee | A61M 1/0064 128/200.23 |
| 5,657,750 A | 8/1997 | Colman et al. | |
| 5,855,203 A * | 1/1999 | Matter | A61L 2/10 128/207.14 |
| 5,857,461 A | 1/1999 | Levitsky et al. | |
| 6,422,240 B1 | 7/2002 | Levitsky et al. | |
| 6,437,316 B1 | 8/2002 | Colman et al. | |
| 6,843,769 B1 | 1/2005 | Gandarias | |
| 6,926,005 B1 | 8/2005 | Colman et al. | |
| 7,503,328 B2 | 3/2009 | Kolobow et al. | |
| 8,074,649 B2 * | 12/2011 | Dhuper | A61M 16/04 128/202.27 |
| 8,323,207 B2 | 12/2012 | Popov et al. | |
| 2003/0078476 A1 | 4/2003 | Hill | |
| 2003/0199807 A1 | 10/2003 | Dent et al. | |
| 2004/0120156 A1 | 6/2004 | Ryan | |
| 2004/0138531 A1 * | 7/2004 | Bonner | A61B 18/1485 600/156 |
| 2004/0210114 A1 * | 10/2004 | Simon | A61B 1/00032 600/185 |
| 2004/0215061 A1 | 10/2004 | Kimmel et al. | |
| 2005/0279354 A1 * | 12/2005 | Deutsch | A61B 1/07 128/200.24 |
| 2007/0088317 A1 * | 4/2007 | Hyde | A61B 17/22 604/500 |
| 2007/0221229 A1 * | 9/2007 | Rahaghi | A61M 16/04 128/207.14 |
| 2010/0113916 A1 * | 5/2010 | Kumar | A61B 5/06 600/424 |
| 2010/0137732 A1 | 6/2010 | Haveri | |
| 2010/0229863 A1 * | 9/2010 | Enk | A61M 16/0096 128/204.21 |
| 2010/0249639 A1 * | 9/2010 | Bhatt | A61B 1/00082 600/546 |
| 2010/0280362 A1 * | 11/2010 | Li | A61M 16/04 600/424 |
| 2011/0178419 A1 | 7/2011 | Wood et al. | |
| 2011/0300505 A1 | 12/2011 | Jessop et al. | |
| 2012/0002427 A1 * | 1/2012 | Moon | F21K 9/00 362/382 |
| 2012/0101343 A1 | 4/2012 | Duffy et al. | |
| 2012/0172664 A1 | 7/2012 | Hayman et al. | |
| 2012/0321509 A1 | 12/2012 | Bak | |
| 2013/0053636 A1 * | 2/2013 | Hayman | A61B 1/00082 600/104 |
| 2013/0092171 A1 | 4/2013 | Sederstrom et al. | |
| 2013/0303849 A1 * | 11/2013 | Allyn | A61B 1/00045 600/109 |
| 2014/0180252 A1 | 6/2014 | Gabriel | |
| 2015/0190649 A1 * | 7/2015 | Gelfand | A61N 5/0601 607/92 |

OTHER PUBLICATIONS

U.S. Office Action dated Aug. 2, 2016, issued in U.S. Appl. No. 14/209,706, 11 pages.

International Search Report and Written Opinion dated May 6, 2015, issued in PCT Patent Application No. PCT/US2015/011818, p pages.

International Search Report and Written Opinion dated Jul. 26, 2016, issued in PCT Patent Application No. PCT/US2016/028949, 10 pages.

* cited by examiner

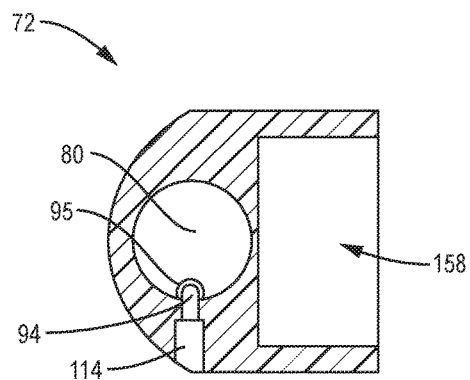
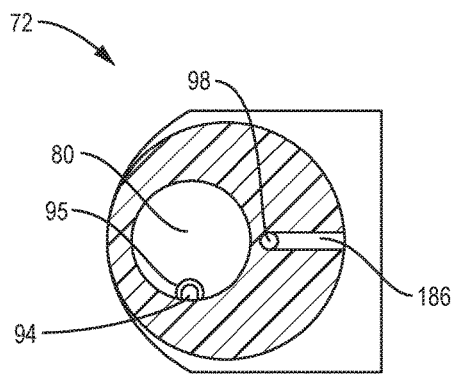
FIG. 21F    FIG. 21G
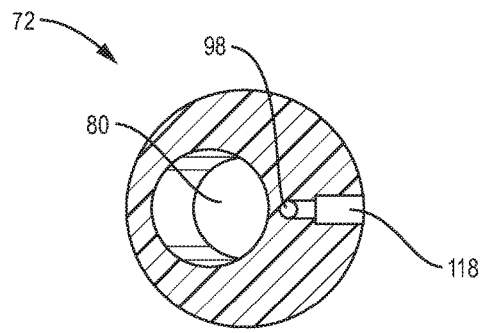
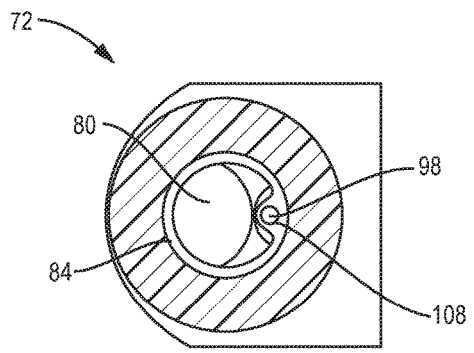
FIG. 21H    FIG. 21I

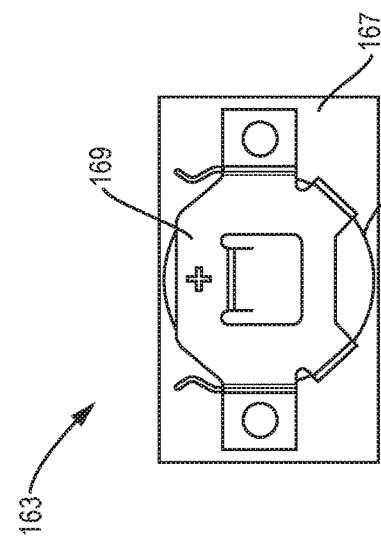
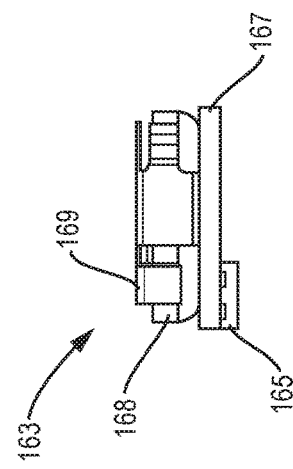
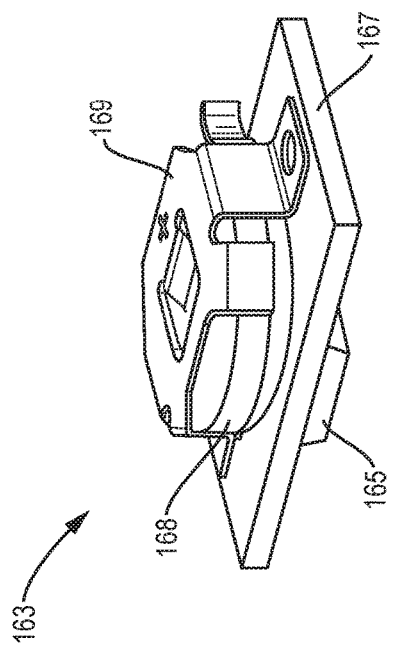
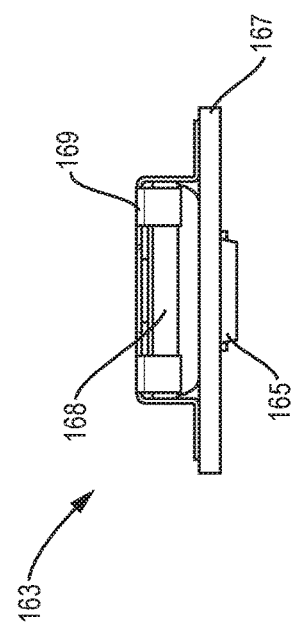

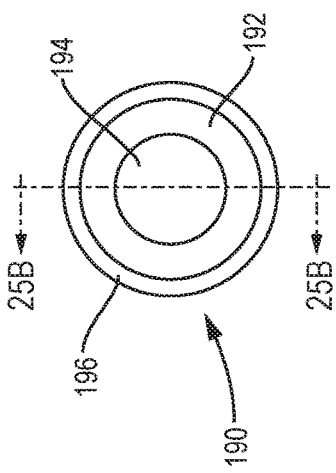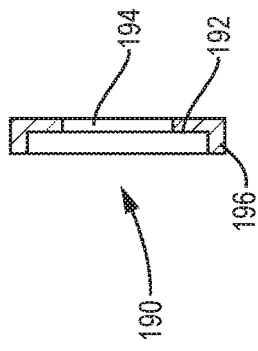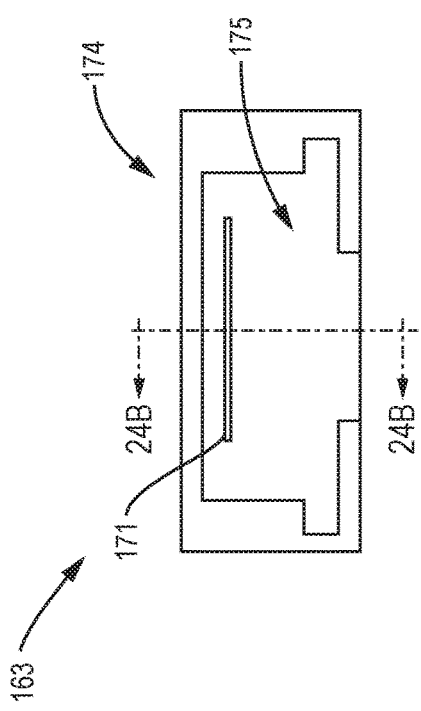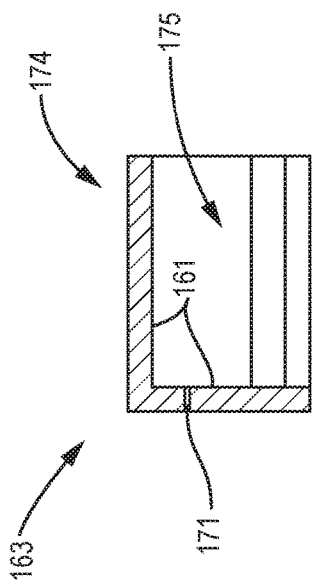

MEDICAL TUBE APPARATUS

CROSS-REFERENCE TO RELATED APPLICATIONS

This application is a continuation-in-part of PCT patent application no. PCT/US2015/011818 filed Jan. 16, 2015, which claims the benefit of U.S. provisional patent application Ser. No. 61/928,685 filed Jan. 17, 2014, the entire disclosures of which are incorporated herein by reference. This application also claims the benefit of U.S. provisional patent application Ser. No. 62/151,899 filed Apr. 23, 2015 and U.S. provisional patent application Ser. No. 62/195,577 filed Jul. 22, 2015, the entire disclosures of which are incorporated herein by reference.

FIELD

This disclosure relates generally to the field of medical devices, and more specifically to a medical tube apparatus and, in certain embodiments, an endotracheal tube apparatus to be used on a human body.

BACKGROUND

Artificial respiration involves assisting or stimulating a person's natural respiration, a metabolic process referring to an exchange of gases within the body by pulmonary ventilation, external respiration and internal respiration. Pulmonary ventilation is achieved through insufflation (e.g. manual or automated) of a person's lungs by causing air or oxygen to flow in and out of a person's lungs, generally when natural breathing has stopped or is otherwise inadequate.

One method of pulmonary ventilation involves intubation, or entubation, which pertains to the insertion of a tube generally into an external orifice of the body. One particular method of intubation is tracheal intubation, in which a flexible plastic tube is inserted into the trachea (windpipe) of a person to provide or maintain an open airway, and to serve as a conduit through which to administer certain drugs via a drug delivery port. Tracheal intubation is often performed in critically injured or anesthetized patients to facilitate pulmonary ventilation and to prevent the possibility of asphyxiation or airway obstruction. Tracheal intubation is most often orotracheal, in which an endotracheal tube is passed through the mouth and voice box (vocal cords) of a person and into the trachea.

During an endotracheal intubation, the person's mouth is opened and the endotracheal tube is inserted down the throat. To better ensure the endotracheal tube is properly positioned, a laryngoscope may be used to bring the vocal cords and larynx into view prior to inserting the endotracheal tube. The tube may then be inserted in the trachea through the vocal cords to the point that an inflation cuff surrounding a distal end portion of the tube rests just below the vocal cords. Finally, after an inflation cuff is inflated to inhibit leakage, a bag valve mask is squeezed adjacent a proximal end of the tube to pass air and/or oxygen to the lungs. A stethoscope may then be used by medical personnel to listen for breathing sounds to ensure proper placement of the tube.

Often endotracheal intubation must be performed away from a clinic and in the field, particularly during a trauma and other emergency situations. Unfortunately, under such adverse conditions, it may not be possible to use a laryngoscope or a stethoscope to ensure proper placement of the endotracheal tube in the trachea, in which case the endotracheal tube may enter the esophagus.

As a result, in addition to a drug delivery port and a cuff inflation port, the endotracheal tube generally includes a sampling port, provided as part of a separate adapter to be connected to the connector of the endotracheal tube, to sample gases of the person being intubated. More particularly, the sampling port may be a carbon dioxide sampling port which is connectable to a carbon dioxide analyzer/monitor (e.g. a capnograph). However, it may be appreciated that in the field such an analyzer/monitor may not always be available for use.

With endotracheal tubes prior to the present disclosure, the drug delivery port and the cuff inflation port include tubing which is spliced from the outside into a side wall of the endotracheal tube. Unfortunately, because the spliced tubing is located between the endotracheal tube and the person's mouth during use, the tubing segments of the ports may be damaged during use, such as being severed by the person's teeth in response to a seizure. Also, the spliced ports may become compressed between the person's mouth and the endotracheal tube, and not function as intended.

What is needed is a tube apparatus, particularly such as an endotracheal tube apparatus, which incorporates various ports which are less susceptible to damage during use of the endotracheal tube. What is also needed is a tube apparatus, such as an endotracheal tube apparatus, which provides visual aid to better ensure proper placement of the endotracheal tube in the trachea. What is also needed is a tube apparatus, such as an endotracheal tube apparatus, which may incorporate one or more sensors, such as to detect one or more physiological parameters applicable to the health state of a person (e.g. detect one or more gases being exhaled by a person (e.g. carbon dioxide) or body temperature). In such a manner, reliance on additional (separate) (equipment which is not always available, particular in the field, may be reduced or eliminated.

SUMMARY

The present disclosure provides medical devices comprising a tube apparatus, which may particularly be an endotracheal tube apparatus, of a medical (respiratory) system. The tube apparatus, such as an endotracheal tube apparatus, may incorporate one or more ports which are less susceptible to damage by a patient during use of the endotracheal tube by virtue of the one or more ports not being spliced into the side wall of the endotracheal tube. The tube apparatus, such as an endotracheal tube apparatus, may also incorporate a lighting apparatus to provide visual aid during endotracheal intubation to better ensure proper placement of the endotracheal tube in the trachea. The tube apparatus, such as an endotracheal apparatus, may also incorporate a sensor apparatus to detect one or more physiological parameters applicable to the health state of a patient to reduce or eliminate reliance on additional (separate) equipment to perform such detection.

In addition to the foregoing benefits, the medical devices comprising a tube apparatus, and more particularly an endotracheal tube apparatus, of a medical (respiratory) system according to the present disclosure, may reduce stack-up of multiple components and associated air leaks occurring there between by combining multiple features into a hub connection fitting of the endotracheal tube apparatus.

In certain embodiments, the present disclosure provides a medical device comprising a tube apparatus including a tube and a hub connection fitting; the tube insertable into a patient; the hub connection fitting connectable to the tube; a central passageway extending through the hub connection fitting and longitudinally with the tube; a plurality of ports joined with the hub connection fitting, the plurality of ports comprising at least a first port and a second port; wherein the first port is operable with a first port passageway, wherein the first port passageway extends through the hub connection fitting and longitudinally with the tube; and wherein the second port is operable with a second port passageway, wherein the second port passageway extends through the hub connection fitting and longitudinally with the tube.

With the tube apparatus, the passageways for the ports are contained in the tube and the hub connection fitting, thus inhibiting a risk that the ports may become damaged once positioned within the trachea of a patient.

In certain embodiments, the present disclosure also provides a medical device comprising an endotracheal tube apparatus including an endotracheal tube and a hub connection fitting; the endotracheal tube insertable into a trachea of a patient; the hub connection fitting connectable to the endotracheal tube; a ventilation passageway extending through the hub connection fitting and along a length of the endotracheal tube; and a plurality of ports joined with the hub connection fitting. The plurality of ports may comprise at least one fluid sampling port and at least one drug delivery port; wherein the fluid sampling port is operable with a fluid sampling passageway, wherein the fluid sampling passageway extends through the hub connection fitting and through a fluid sampling lumen of the endotracheal tube and wherein the drug delivery port is operable with a drug delivery passageway, wherein the drug delivery passageway extends through the hub connection fitting and through a drug delivery lumen of the endotracheal tube. In certain embodiments, the plurality of ports may further comprise at least one cuff inflation port or an additional drug delivery port. The cuff inflation port may be present for adult devices, and removed for pediatric or neonatal devices.

In certain embodiments, the fluid sampling passageway extends through a fluid sampling port tubing segment which connects the fluid sampling port to the hub connection fitting; and the drug delivery passageway extends through a drug delivery port tubing segment which connects the drug delivery port to the hub connection fitting.

In certain embodiments, the fluid sampling port tubing segment is located in a first counterbore of the hub connection fitting; and the drug delivery port tubing segment is located in a second counterbore of the hub connection fitting.

In certain embodiments, at least one of the fluid sampling port tubing segment and the drug delivery port tubing segment is at least one of interference fit, adhesively bonded and welded to the hub connection fitting.

In certain embodiments, the fluid sampling port includes a fluid sampling port connector to connect the fluid sampling port to an analyzer to detect a presence of carbon dioxide gas in a fluid sample comprising one or more gases exhales from the patient.

In certain embodiments, the hub connection fitting comprises a fluid sampling passageway connector which connects with the fluid sampling passageway of the endotracheal tube; and a drug delivery passageway connector which connects with the drug delivery passageway of the endotracheal tube.

In certain embodiments, the fluid sampling passageway connector comprises a male connector portion which is located in a fluid sampling lumen of the endotracheal tube which provides the fluid sampling passageway of the endotracheal tube; and the drug delivery passageway connector comprises a male connector portion which is located in a drug delivery lumen of the endotracheal tube which provides the drug delivery passageway of the endotracheal tube.

In certain embodiments, the fluid sampling passageway connector is at least one of interference fit, adhesively bonded and welded within the fluid sampling lumen of the endotracheal tube; and the drug delivery passageway connector is at least one of interference fit, adhesively bonded and welded within the drug delivery lumen of the endotracheal tube.

In certain embodiments, the plurality of ports further comprise at least one cuff inflation port; and wherein the cuff inflation port in operable with a cuff inflation passageway, wherein the cuff inflation passageway extends through the hub connection fitting and through a cuff inflation lumen of the endotracheal tube.

In certain embodiments, the cuff inflation passageway extends through a cuff inflation port tubing segment which connects the cuff inflation port to the hub connection fitting;

In certain embodiments, the cuff inflation port tubing segment is located in a counterbore of the hub connection fitting.

In certain embodiments, the cuff inflation port tubing segment is at least one of interference fit, adhesively bonded and welded to the hub connection fitting.

In certain embodiments, the hub connection fitting comprises a cuff inflation passageway connector which connects with the cuff inflation passageway of the endotracheal tube.

In certain embodiments, the cuff inflation passageway connector comprises a male connector portion which is located in a cuff inflation lumen of the endotracheal tube which provides the cuff inflation passageway of the endotracheal tube.

In certain embodiments, the cuff inflation passageway is at least one of interference fit, adhesively bonded and welded within the cuff inflation lumen of the endotracheal tube.

In certain embodiments, the hub connection fitting includes cylindrical connector portion adapted to be inserted into a respirator tube of a respirator means.

In certain embodiments, the medical device further comprises a lighting apparatus. The lighting apparatus may comprise a light source and a battery.

In certain embodiments, the medical device further comprises a camera.

In certain embodiments, the present disclosure also provides a medical device comprising an endotracheal tube apparatus including an endotracheal tube and a hub connection fitting; the endotracheal tube insertable into a trachea of a patient; the hub connection fitting connectable to the endotracheal tube; a ventilation passageway extending through the hub connection fitting and along a length of the endotracheal tube; and a plurality of ports joined with the hub connection fitting. The plurality of ports may comprise at least one fluid sampling port, at least one drug delivery port, and at least one cuff inflation port; wherein the fluid sampling port is operable with a fluid sampling passageway, wherein the fluid sampling passageway extends through the hub connection fitting and through a fluid sampling lumen of the endotracheal tube; wherein the drug delivery port is operable with a drug delivery passageway, wherein the drug delivery passageway extends through the hub connection fitting and through a drug delivery lumen of the endotracheal tube; and wherein the cuff inflation port in operable with a cuff inflation passageway, wherein the cuff inflation passageway extends through the hub connection fitting and through a cuff inflation lumen of the endotracheal tube.

In certain embodiments, the present disclosure also provides a method of forming a medical device comprising: providing an elongated tube having a plurality of lumens; providing a hub connection fitting including a plurality of male connectors; connecting the hub connection fitting and the tube such that each male connector of the plurality of male connectors is inserted into and occupies a different lumen of the plurality of lumens of the tube; wherein the plurality of lumens comprise at least a central lumen; a first secondary lumen and a second secondary lumen; wherein, upon connecting the hub connection fitting and the tube, a central passageway is formed which extends through the hub connection fitting and longitudinally through the central lumen of the tube; a first port passageway is formed which extends through the hub connection fitting and longitudinally through the first secondary lumen of the tube; and a second port passageway is formed which extends through the hub connection fitting and longitudinally through the second secondary lumen of the tube.

In certain embodiments, the present disclosure provides a medical device comprising an endotracheal tube apparatus including an endotracheal tube and a hub connection fitting; the endotracheal tube insertable into a trachea of a patient; the hub connection fitting connectable to the endotracheal tube; a ventilation passageway extending through the hub connection fitting and along a length of the endotracheal tube; and the hub connection fitting including a light emitting device.

In certain embodiments, the hub connection fitting contains the light emitting device.

In certain embodiments, the hub connection fitting comprises a hub connection fitting body; the light emitting device comprises a light-source module; and the light source module is contained in the hub connection fitting body.

In certain embodiments, the light source module comprises at least one light-emitting diode mounted to a printed circuit board, and a battery.

In certain embodiments, the light source module comprises a removable non-conductive liner which is arranged to inhibit a formation of an electrical connection between the at least one light emitting diode and the battery.

In certain embodiments, the light source module comprises a housing which contains the battery, the printed circuit board and the removable non-conductive liner.

In certain embodiments, a second passageway extends along the length of the endotracheal tube parallel with the ventilation passageway; and the light-emitting device is arranged to direct light down the second passageway.

In certain embodiments, the light-emitting device comprises a tubular light guide; and the second passageway contains the tubular light guide.

In certain embodiments, the light-emitting device comprises a light source; the hub connection fitting includes the light source of the light emitting device; and the light source and the tubular light guide are arranged such that the light source provides light along a length of the tubular light guide.

In certain embodiments, the light source and the tubular light guide are arranged such that the light source provides light into the tubular light guide without being reflected.

In certain embodiments, the light source and the tubular light guide are arranged such that the light source provides light into the tubular light guide after the light has been reflected.

In certain embodiments, the light source and the tubular light guide are arranged such that the light source provides light into the tubular light guide after the light has been reflected 90 degrees.

In certain embodiments, the second passageway is defined by a side wall; and when the endotracheal tube is bent, at least a portion of the tubular light guide is slidable along the side wall.

In certain embodiments, the second passageway is at least one of a fluid sampling passageway, a drug delivery passageway; and a cuff inflation passageway.

In certain embodiments, at least one of a fluid sampling port, a drug delivery port and a cuff inflation port joined with the hub connection fitting; and the at least one of a fluid sampling port, a drug delivery port and a cuff inflation port is operable with the second passageway.

In certain embodiments, the secondary passageway is a cuff inflation passageway; the at least one of a fluid sampling port, a drug delivery port and a cuff inflation port joined with the hub connection fitting is a cuff inflation port joined with the hub connection fitting; and the cuff inflation port is operable with the cuff inflation passageway.

In certain embodiments, the present disclosure provides a medical device comprising an endotracheal tube apparatus including an endotracheal tube and a hub connection fitting; the endotracheal tube insertable into a trachea of a patient; the hub connection fitting connectable to the endotracheal tube; a ventilation passageway extending through the hub connection fitting and along a length of the endotracheal tube; a secondary passageway within the ventilation passageway arranged such that the secondary passageway is in fluid communication with the ventilation passageway; and the secondary passageway having a side wall formed unitarily with a sidewall of the ventilation passageway as a single piece monolithic structure.

In certain embodiments, the hub connection fitting is formed of thermoplastic, such as polyethylene, polypropylene, polyamide or polyacetal, by injection molding.

In certain embodiments, the present disclosure provides a medical device comprising an endotracheal tube apparatus including an endotracheal tube and a hub connection fitting; the endotracheal tube insertable into a trachea of a patient; the hub connection fitting connectable to the endotracheal tube; a ventilation passageway extending through the hub connection fitting and along a length of the endotracheal tube; and the hub connection fitting including a sensor apparatus configured to detect one or more respiration gases of the patient.

In certain embodiments, the hub connection fitting contains the sensor apparatus.

In certain embodiments, the hub connection fitting comprises a hub connection fitting body; the sensor apparatus comprises a sensor module; and the sensor module is contained in the hub connection fitting body.

In certain embodiments, the sensor module comprises a printed circuit board and a battery.

In certain embodiments, the sensor module comprises a removable non-conductive liner which is arranged to inhibit a formation of an electrical connection.

In certain embodiments, the sensor module comprises a housing which contains the battery, the printed circuit board and the removable non-conductive liner.

In certain embodiments, the sensor apparatus comprises a sensor, such as a carbon dioxide sensor.

In certain embodiments, the sensor comprises a capnography sensor, a spectroscopic sensor, a light sensor and/or an infrared sensor.

In certain embodiments, the sensor comprises a light emitter and a light detector.

In certain embodiments, the hub connection fitting comprises at least one of a processor, a computer readable storage medium, a communication element, and an output display which each operate with the sensor.

In certain embodiments, the communication element comprises at least one of a transmitter and a receiver.

In certain embodiments, the output display comprises at least one of a liquid crystal display, a light-emitting diode, a gas plasma display and a cathode ray tube.

In certain embodiments, the sensor apparatus is configured to wirelessly communicate with at least one remote electronic device.

In certain embodiments, the senor apparatus is configured to wirelessly communicate with the at least one remote electronic device on a network.

In certain embodiments, the at least one remote electronic device comprises at least one of a desktop computer, a portable computer, a laptop computer, a notebook computer, a netbook computer, a personal digital assistant computer, a wearable computer, a phone computer or handheld computer.

In certain embodiments, the sensor apparatus comprises a sensor; and at least one of the sensor apparatus and the at least one remote electronic device is configured to convert a signal from the sensor to an exhaled gas concentration value by an algorithm.

In certain embodiments, at least one of the sensor apparatus and the at least one remote electronic device is configured to output a visual representation of the exhaled gas concentration value to an output display.

FIGURES

The above-mentioned and other features of this disclosure, and the manner of attaining them, will become more apparent and better understood by reference to the following description of embodiments described herein taken in conjunction with the accompanying drawings, wherein:

FIG. 21F is a transverse cross sectional view of the hub connection fitting of FIG. 20A taken along line 21F-21F of FIG. 21E;

FIG. 21G is a transverse cross sectional view of the hub connection fitting of FIG. 20A taken along line 21G-21G of FIG. 21E;

FIG. 21H is a transverse cross sectional view of the hub connection fitting of FIG. 20A taken along line 21H-21H of FIG. 21E;

FIG. 21I is a transverse cross sectional view of the hub connection fitting of FIG. 20A taken along line 21I-21I of FIG. 21E;

FIG. 23A is an assembled perspective view of a lighting device of a light source module of the hub connection fitting of FIG. 20A;

FIG. 23B is a top view of the lighting device of FIG. 23A;

FIG. 23C is a first side view of the lighting device of FIG. 23A;

FIG. 23D is a second side view of the lighting device of FIG. 23A;

FIG. 24A is a first side view of a housing for the lighting device for the light source module of FIG. 23A;

FIG. 24B is a cross sectional side view of the housing of FIG. 24A taken along line 24B-24B of FIG. 24A;

FIG. 25A is a top view of an endotracheal tube connector of the hub connection fitting of FIG. 20A; and FIG. 25B is a longitudinal cross-sectional side view of the endotracheal tube connector of FIG. 25A taken along line 25B-25B of FIG. 25A.

DETAILED DESCRIPTION

Figure 1:
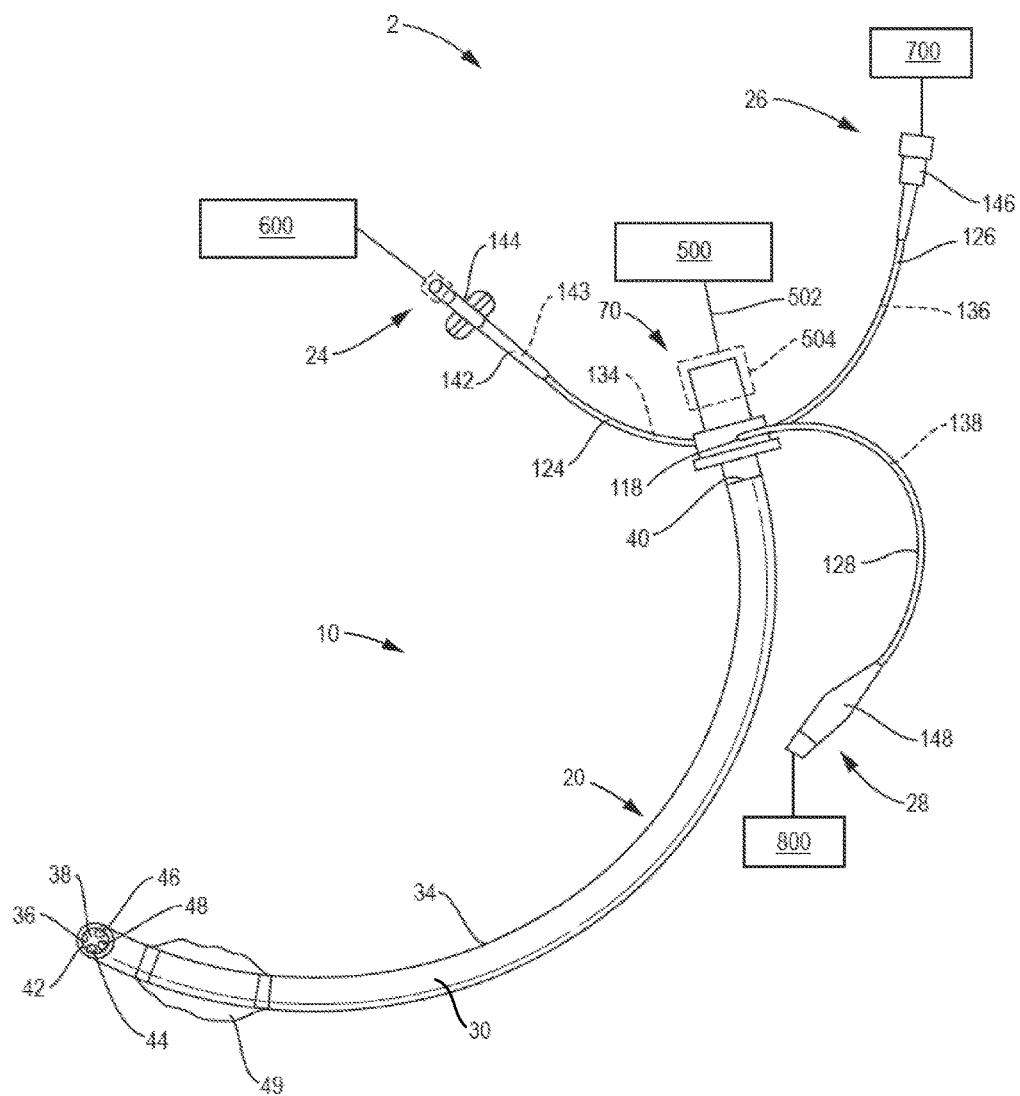
FIG. 1 is a side view of a medical system including a medical device comprising a tube apparatus, and more particularly an endotracheal tube apparatus, according to the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art. Furthermore, throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this disclosure as suitable. In other words, features between the various exemplary embodiments described herein are interchangeable as suitable, and not exclusive.

Referring now to FIGS. 1-5, there is shown a medical device 10 comprising a tube apparatus 20, and more particularly an endotracheal tube apparatus 20 of a medical (respiratory) system 2 according to the present disclosure. While a remainder of the disclosure may refer to the tube apparatus as being an endotracheal tube apparatus 20, particularly for single-use (disposable) applications, it should be understood that the present disclosure is not limited to an endotracheal tube apparatus 20, and the present tube apparatus may have other medical applications, as well as non-medical applications, other that of endotracheal tube apparatus 20. While endotracheal tube apparatus 20 may be described herein for oral intubation, apparatus 20 may also be used for tracheal intubation (e.g. cricothyrotomy tube, tracheostomy tube) and nasal intubation.

As shown, the endotracheal tube apparatus 20 comprises a flexible, elongated, hollow endotracheal tube 30, which may be extruded (thermoplastic) tubing having a constant profile along its length, to be inserted into the trachea of a human host, such as a patient. Exemplary thermoplastic polymer compositions may include plasticized polyvinyl chloride and thermoplastic elastomers. As such, in certain embodiments, the endotracheal tube 30 may have a length in a range of 7.5 cm to 50 cm (including all ranges and increments there between); and more particularly in a range of 17 cm to 23 cm (including all ranges and increments there between). As shown, endotracheal tube 30 is cylindrical, with a constant diameter, however in other embodiments endotracheal tube 30 may not necessarily be cylindrical or have a constant diameter.

Endotracheal tube 30 is preferably light transmissive to visible light and substantially transparent. As used herein, substantially transparent may be understood as providing integral transmission of at least 60% of incident light in the visible spectrum (about 400-700 nm wavelength), and more preferably at least 70% of incident light in the visible spectrum, and even more preferably, at least 80% or moreover at least 90% of incident light in the visible spectrum. Also, substantially transparent may be understood to include translucent in accordance with the above.

As used herein, an elastomer may be characterized as a material that has an elongation at 23° C. of at least 100%, and which, after being stretched to twice its original length and being held at such for one minute, may recover in a range of 50% to 100% within one minute after release from the stress. More particularly, the elastomer may recover in a range of 75% to 100% within one minute after release from the stress, and even more particularly recover in a range of 90% to 100% within one minute after release from the stress. The elastomer may be comprised of any polymer, including natural or synthetic polymers, and thermoplastic or thermoset polymers. Thus, the elastomer may be either a natural or synthetic elastomer. The elastomer may comprise, essentially consist of or consist of natural or synthetic rubber.

Endotracheal tube 30 has an outer cylindrical side wall 32 having an outer surface 34 an inner surface 36. In certain embodiments, the endotracheal tube 30 may have an outer diameter OD in a range of 5 mm to 15 mm (including all ranges and increments there between), and more particularly in a range of 9 mm to 13 mm (including all ranges and increments there between). The thickness of the outer cylindrical side wall 32 may be in a range from 0.75 mm to 3 mm (including all ranges and increments there between) and more particularly in a range of 1 mm to 2 mm (including all ranges and increments there between).

Endotracheal tube 30 includes a centrally disposed ventilation passageway 38, in the form of a lumen, which extends along the length of the endotracheal tube 30 from a proximal end opening 40 of the endotracheal tube 30 to a distal end opening 42 of the endotracheal tube 30. As shown, the ventilation passageway 38 shares a common longitudinal (center) axis 41 with the endotracheal tube 30. Ventilation passageway 38 may be understood as the primary passageway for tracheal intubation and subsequent use of a respirator apparatus 500, such as a bag valve mask or a mechanical ventilator as known in the art connected to endotracheal tube apparatus 20 to provide mechanical ventilation/respiration to the patient.

Respirator apparatus 500 may also include an impedance threshold device (ITD) as known in the art that selectively prevents unnecessary air from enter the chest/lungs of a patient during the chest wall recoil phase of cardiopulmonary resuscitation (CPR). The ITD may be used in conjunction with the bag valve mask as known in the art. Use of the ITD device results in greater vacuum (negative pressure) in the chest/lungs during the chest wall recoil phase. An exemplary ITD is the ResQPOD impedance threshold device. The ITD maintains lower airway pressure and reduces the pressure inside the patient's chest. This reduced pressure draws more blood back to the heart during the decompression phase of CPR. As a result, a greater volume of blood may flow out of the heart during the next compression, which may improve overall blood circulation as compared to standard CPR.

The maximum inner diameter ID of the ventilation passageway 38 may be in a range of 3 mm to 13 mm (including all ranges and increments there between), and more particularly in a range of 7 mm to 11 mm (including all ranges and increments there between).

In addition, endotracheal tube 30 includes a plurality of secondary passageways 44, 46 and 48, all provided by lumens, which have (semi) cylindrical side walls 54, 56 and 58 which are formed unitary (i.e. formed as a single piece monolithic) with the outer cylindrical side wall 32, with the cylindrical side walls 54, 56 and 58. As shown, the semi cylindrical side walls 54, 56 and 58 have a circumference which extends over an arc of approximately 200 degrees. However, the circumference of the arc may range from, for example, 180 degrees to 330 degrees (including all ranges and increments there between), and more particularly 200 degrees to 300 degrees (including all ranges and increments there between). While all the secondary passageways 44, 46 and 48 are shown to have the same cross-sectional profile (circular) and size, they may have different profiles and sizes.

As shown, the secondary passageways 44, 46 and 48 may be arranged 90 degrees apart from one another on the outer cylindrical side wall 32 and extend parallel with ventilation passageway 38 in endotracheal tube 30. As shown, all of the ventilation passageway 38 and the secondary passageways 44, 46 and 48 have a different longitudinal axis (i.e. none of the ventilation passageway 38 and secondary passageways 44, 46 and 48 are coaxial), and the axis of secondary passageways 44, 46 and 48 are parallel with the axis of ventilation passageway 38. Cylindrical side walls 54, 56 and 58 may have a thickness in a range from 0.5 mm to 2 mm (including all ranges and increments there between) and more particularly in a range of 0.75 mm to 1.5 mm (including all ranges and increments there between).

Figure 1A:
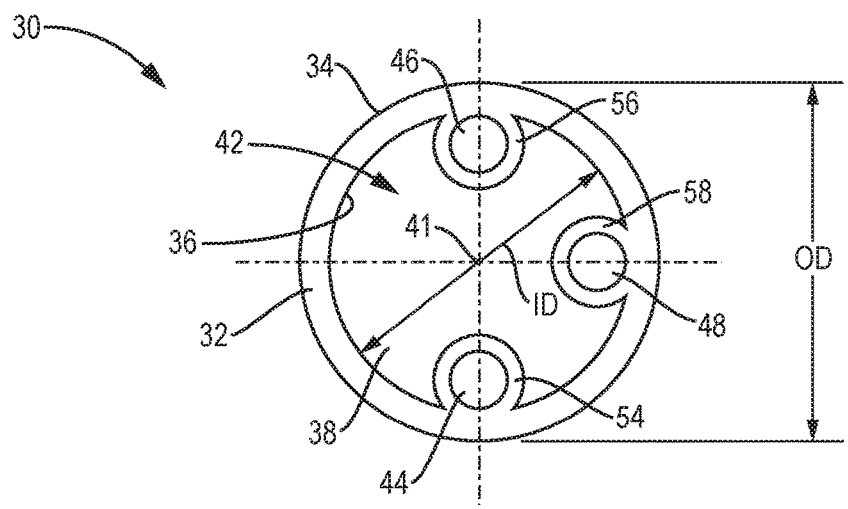
FIG. 1A is an enlarged distal end view of the endotracheal tube apparatus of FIG. 1.

As shown in FIG. 1A, in certain embodiments the secondary passageways 44, 46 and 48 may not be formed within the outer cylindrical side wall 32, but rather adjacent thereto, as placing the secondary passageways 44, 46 and 48 within the confines of the outer cylindrical side wall 32 may locally weaken the outer cylindrical side wall 32. Furthermore, as the proximal end of the endotracheal tube 30 seals with a hub connection fitting 70 as further described herein, maintaining the thickness of outer cylindrical side wall 32 uniformly around the ventilation passageway 38 may provide a more stable seal. In such case, as shown, the secondary passageways 44, 46, 48 and the inner walls thereof 54, 56, 58 thereof will narrow the ventilation passageway 38 in certain locations along the length of the ventilation passageway 38 in the form of a semi-circular/semi-cylindrical protuberance into the ventilation passageway 38.

Figure 1B:
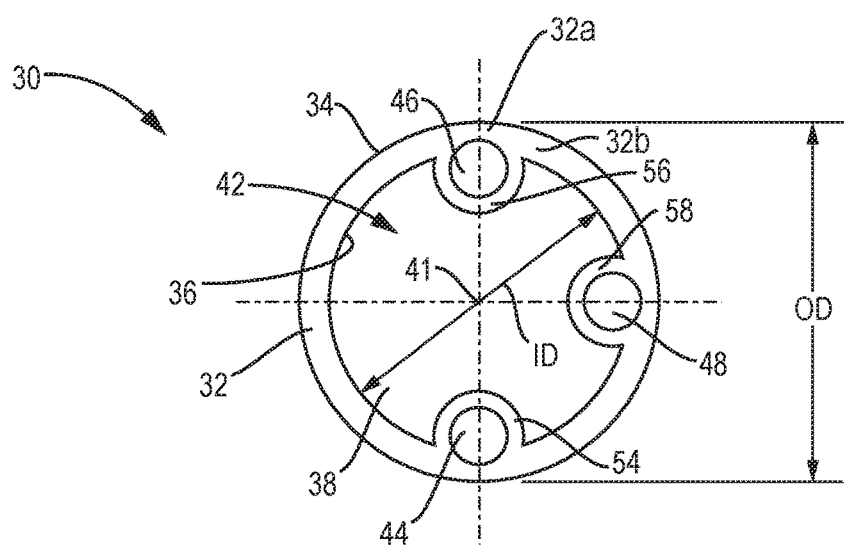
FIG. 1B is an enlarged distal end view of another embodiment of the endotracheal tube apparatus.

However, in certain embodiments, as shown in FIG. 1B, one or more of the secondary passageways 44, 46 and 48 may reduce the thickness of the outer cylindrical side wall 32 (shown at location 32a) to no less than 60% (and preferably no less than 70% and more preferably no less than 80% and even more preferably no less than 90%) of the thickness of the outer cylinder side wall 32 adjacent to the secondary passageways 44, 46 and 48 (shown at location 32b) located between the secondary passageways 46 and 48.

As explained in greater detail below, secondary passageway 44 is a fluid sampling passageway in fluid communication with a fluid sampling port 24 of the endotracheal tube apparatus 20, while secondary passageway 46 is a drug delivery passageway in fluid communication with a drug delivery port 26 and secondary passageway 48 is a cuff inflation passageway in fluid communication with a cuff inflation port 28. As shown, the overall inner diameter and radius of the secondary passageways 44, 46, 48 is smaller than the overall inner diameter and radius of the ventilation passageway 38, and in a range of 10%-50% of the inner diameter and radius of the ventilation passageway 38 (including all ranges and increments there between) and more particularly in a range of 20%-40% (including all ranges and increments there between) of the inner diameter and radius of the ventilation passageway 38, such as 25-35% of the inner diameter and radius of the ventilation passageway 38 (including all ranges and increments there between).

In addition to endotracheal tube 30, endotracheal apparatus 20 further comprises hub connection fitting 70 that operatively connects the endotracheal tube 30 to respirator apparatus 500. The hub connection fitting 70 comprises a (main) body 72, which may be formed of injection molded thermoplastic, such as polypropylene, polyethylene, polyamide and polyacetal. The hub connection fitting 70 comprises a body 72 having a proximal body portion 74, which provides a male connector portion shown to be cylindrical, and a distal body portion 76, which provides a male connector portion shown to be cylindrical, separated by an intermediate/middle body portion 78. Hub connection fitting 70 further comprises a ventilation passageway 80 which extends through the proximal body portion 74, intermediate/middle body portion 78 and distal body portion 76. Ventilation passageway 80 is to provide fluid communication between ventilation passageway 38 of endotracheal tube 30 and respirator apparatus 500.

The outer diameter of the proximal body portion 74 of the hub connection fitting 70 is dimensioned to be inserted into a passageway 502 of a respirator tube 504 of respirator apparatus 500 and interference (frictionally) fit with the inside diameter of the side wall 506 thereof. The respirator tube 504 may contact against annular lip/shoulder 82 of intermediate/middle portion 78.

In addition to ventilation passageway 80, hub connection fitting 70 includes three secondary passageways 94, 96 and 98 arranged to connect and provide fluid communication with secondary passageways 44, 46 and 48 of endotracheal tube 30. As such, secondary passageway 94 defines a portion of the fluid (exhaled gas(es) from the patient) sampling passageway in fluid communication with fluid sampling port 24 of the endotracheal tube apparatus 20, while secondary passageway 96 defines a portion of the drug delivery passageway in fluid communication with drug delivery port 26 and secondary passageway 98 defines a portion of the cuff inflation passageway in fluid communication with cuff inflation port 28.

As shown, the secondary passageways 94, 96 and 98 are shown to have an L-shape including a 90 degree bend/angle A. However, while angle A is shown at 90 degrees, the shape and/or angle may be different in other embodiments. For example, angle A may be in a range of 10 degrees to 170 (e.g. 20 degrees to 160 degrees, 30 degrees to 150 degrees, 45 degrees to 135 degrees, 30 degrees to 90 degrees, 90 degrees to 160 degrees, 45 degrees to 90 degrees, 90 degrees to 135 degrees) relative to the longitudinal axis, with an acute angle A being towards the distal body portion 76 and an obtuse angle A being towards the proximal body portion 74. For example, as shown in phantom, an obtuse angle A' is shown at 135 degrees. The angle A may be made obtuse particularly to make it easier to pass other medical devices down the secondary passageways 94, 96 and 98.

Longitudinal (parallel) to the longitudinal axis of the hub connection fitting 70, within the confines of intermediate/middle portion 78 and distal body portion 76, secondary passageways 94, 96 and 98 may be defined by cylindrical side walls 95, 97 and 99, respectively, which each form a semi-cylindrical section which is shown to narrow the ventilation passageway 80. The distal end of each secondary passageway 94, 96 and 98, and more particularly of side walls 95, 97 and 99 may be defined by a distal male connector portion 104, 106, 108 of the hub connection fitting 70, which is cylindrical and dimensioned to be inserted into secondary passageways 44, 46 and 48, respectively, of endotracheal tube 30 and interference (frictionally) fit with the inside diameter of the side walls 54, 56 and 58, respectively. As shown, any or all of the male connector portions 104, 106, and 108 may be formed as one piece with the hub connection fitting body 72. Alternatively, such may be formed separately from the hub connection fitting body 72 as separate pieces. In such regard, the male connector portions 104, 106, and 108 may be made of metal or a plastic different than that of the hub connection fitting body 72 for increased strength. Such may be welded to the hub connection fitting body 72 by threaded engagement and/or ultrasonic welding, similar to threaded insert.

Thus, the hub connection fitting 70 includes a fluid sampling passageway connector (provided by male connector portion 104) which connects to the secondary passageway 44 of the endotracheal tube 30 for fluid sampling; a drug delivery passageway connector (provided by male connector portion 106) which connects to the secondary passageway 46 of the endotracheal tube 30 for drug delivery; and a cuff inflation connector (provided by male connector portion 108) which connects to the secondary passageway 48 of the endotracheal tube 30 for cuff inflation. Further, the endotracheal tube 30 is to preferably contact and butt against annular lip/shoulder 84 of distal body portion 76. In the foregoing manner, all of the passageways may be sealed between endotracheal tube 30 and hub connection fitting 70 with a fluid (air) tight seal, i.e. a hermetic seal. In certain alternative embodiments, the distal end of each secondary passageway 94, 96 and 98 defined by a male connector portion 104, 106, 108 may be adhesively bonded with the inside diameter of the side walls 54, 56 and 58, respectively, and the endotracheal tube 30 in contact against annular lip/shoulder 84 of distal body portion 76 may also be adhesively bonded with an adhesive.

Figure 2:
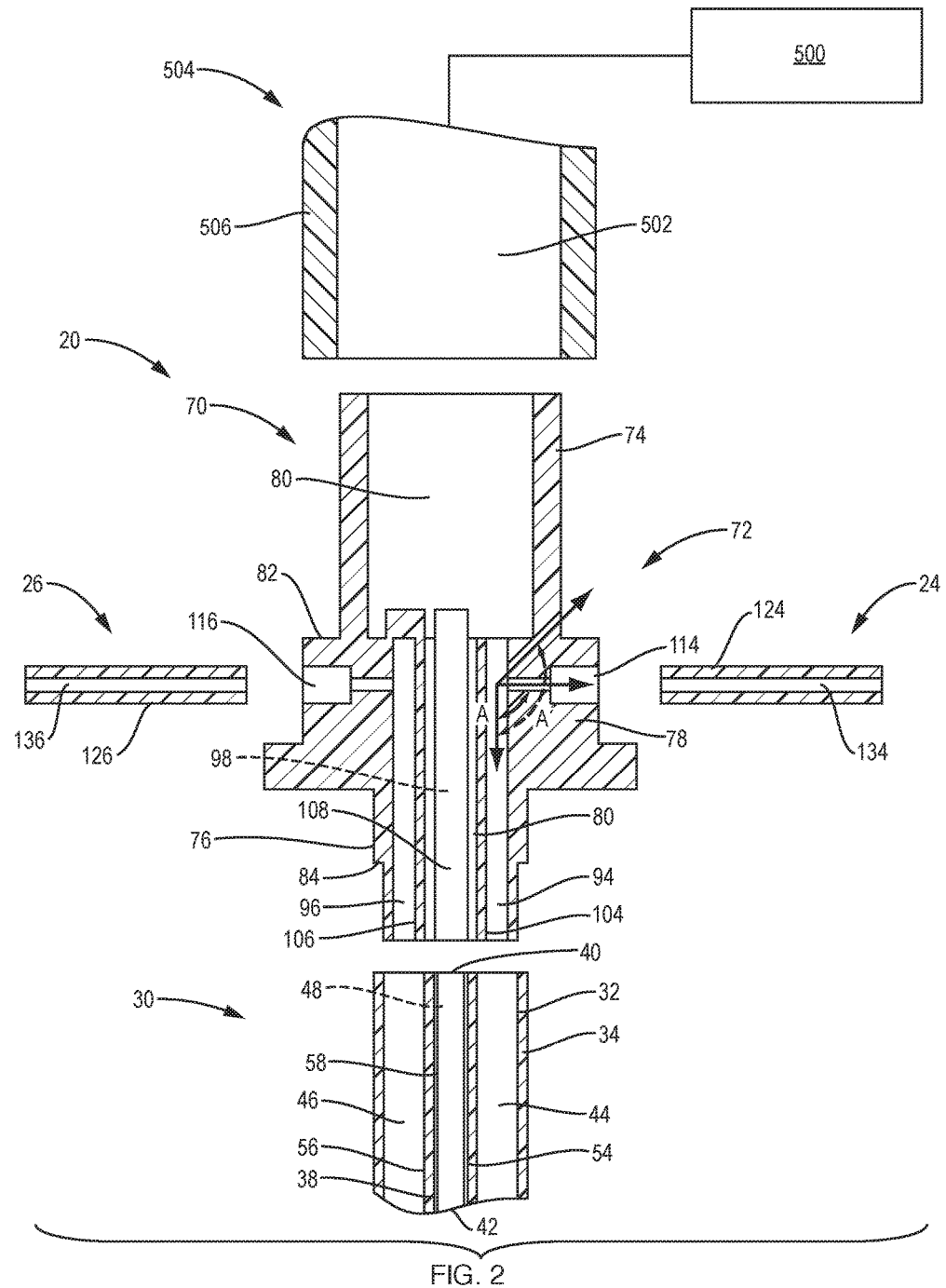
FIG. 2 is an exploded longitudinal cross-sectional side view of the endotracheal tube apparatus of FIG. 1.
Figure 2A:
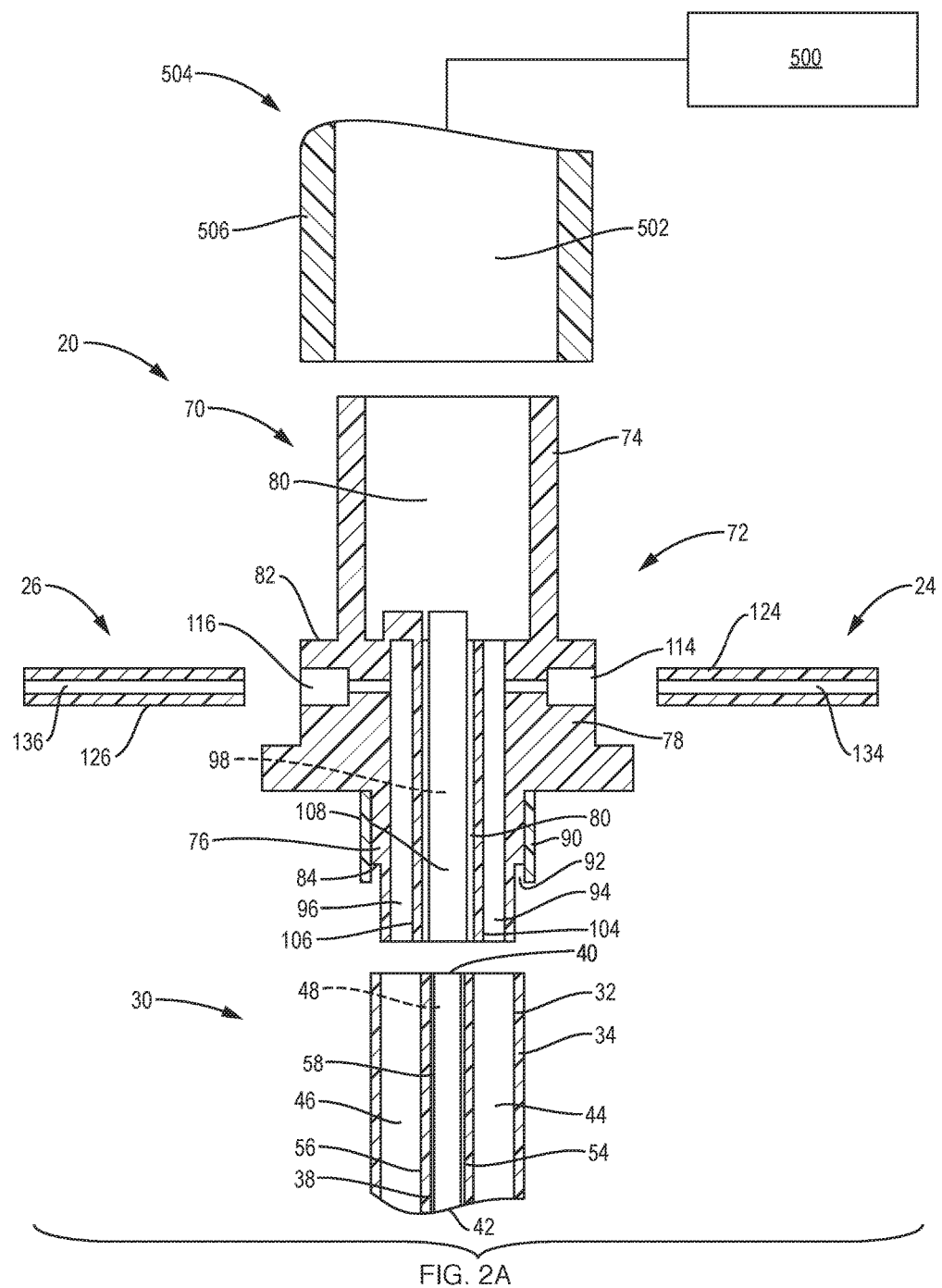
FIG. 2A is an exploded longitudinal cross-sectional side view of another embodiment of the endotracheal tube apparatus.
Figure 3:
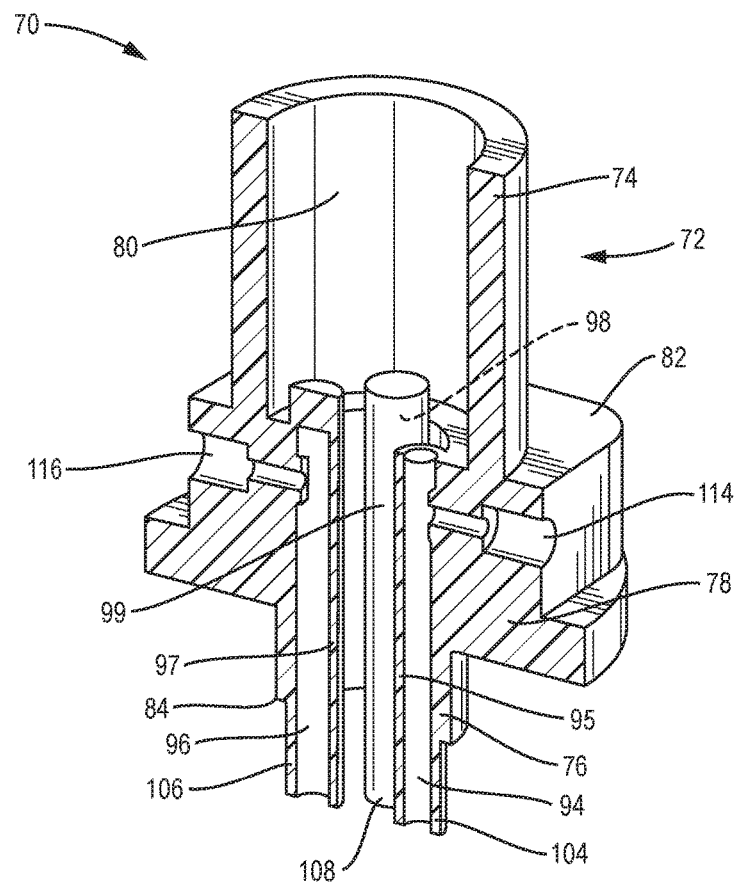
FIG. 3 is a longitudinal cross-sectional perspective view of a hub connection fitting of the endotracheal tube apparatus of FIG. 1.
Figure 4:
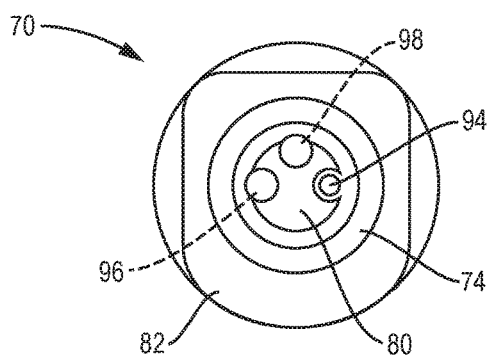
FIG. 4 is a top view of the hub connection fitting of the endotracheal tube apparatus of FIG. 1.
Figure 5:
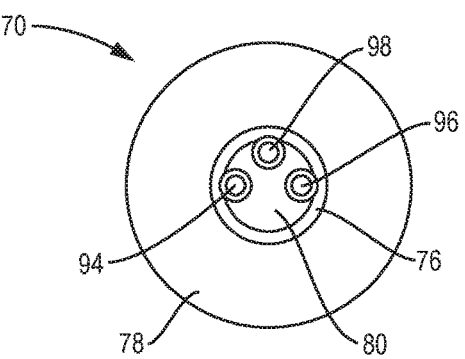
FIG. 5 is a bottom view of the hub connection fitting of the endotracheal tube apparatus of FIG. 1.

In certain embodiments, the distal end of each secondary passageway 94, 96 and 98 defined by a male connector portion 104, 106, 108 may be also be welded with the inside diameter of the side walls 54, 56 and 58, respectively, and proximal end of the endotracheal tube 30 in contact against annular lip/shoulder 84 of distal body portion 76 may also be welded thereto. A thin membrane (e.g. an adhesive bonding tape strip) may also overlie the butt joint around the diameter thereof. Alternatively, as shown in FIG. 2A, an annular ring 90 may overlie distal body portion 76 and be at least one of interference fit, adhesive bonded and welded thereto. Alternatively, annular ring 90 may be provided as part of the body 72 of hub connection fitting 70, i.e. as a single piece. As shown, a recess 92 is now formed at the distal end of distal body portion 76 into which endotracheal tube 30 may be located and at least one of interference fit, adhesive bonded and welded thereto. It should be understood that any combination of interference fits, adhesive bonding and welding may be used for any of the connections alone or in conjunction with another joining method.

The proximal end of each secondary passageway 94, 96, 98 may include a counter-bore 114, 116, 118. Counter-bore 114 is configured to receive the distal end portion of tubing segment 124, which may be an extruded tubing segment, in fluid communication with the fluid sampling port 24. Counter-bore 116 is configured to receive the distal end portion of tubing segment 126, which may be an extruded tubing segment, in fluid communication with the drug delivery port 26. Counter-bore 118 (on the backside of the structure, same type of counter-bore as 114 and 116) is configured to receive the distal end portion of tubing segment 128, which may be an extruded tubing segment, in fluid communication with the cuff inflation port 28. In order to join the two components together, the distal end portion of tubing segment 124, 126, 128 may be interference fit with counter-bore 114, 116, 118. Alternatively, or in conjunction with the interference fit, the distal end portion of tubing segment 124, 126, 128 may be adhesive bonded with counter-bore 114, 116, 118 with an adhesive and/or the distal end portion of tubing segment 124, 126, 128 may be welded with counter-bore 114, 116, 118.

As shown, the tubing segment 124 in fluid communication with the fluid sampling port 24 includes a passageway (lumen) 134 which forms part of the fluid sampling passageway which extends through hub connection fitting 70 (as secondary passageway 94) and endotracheal tube 30 (as secondary passageway 44). As shown, the proximal end of tubing segment 124 is connected to fluid sampling port 24, which comprises a filter 142 and fluid sampling port threaded connector 144, which connects fluid sampling port 24 to an analyzing/monitoring apparatus 600. More particularly, fluid sampling port 24 may be a carbon dioxide sampling port, and analyzing/monitoring apparatus 600 may be a carbon dioxide analyzer/monitor (e.g. a capnograph). Filter 142 may be particularly suited to separate liquids (e.g. saliva) from the gases (e.g. carbon dioxide) exhaled by the patient, such that the gases therein may be analyzed by a gas analyzer, such as a capnograph, which may detect a presence of carbon dioxide therein. In other embodiments, fluid sampling port 24 may be a sampling port which provides a liquid (e.g. saliva) sample for analysis, with or without a gas sample for analysis. In certain embodiments, fluid sampling port 24 may include colorimetric paper 143 to detect a presence of carbon dioxide in the fluid sample exhaled from the patient. The colorimetric paper 143 (e.g. Kangaroo™ $CO_2$ colorimetric paper from Covidien) may be wrapped around filter 142.

With use of endotracheal tube apparatus 20, gases exhaled by the patient may enter secondary passageway 44 of endotracheal tube 30 at the distal end opening 42 of endotracheal tube 30, and thereafter flow through secondary passageway 94 of hub connection fitting 70 and passageway 134 of tubing segment 124, and thereafter through fluid sampling port threaded connector 144, filter 142 and into analyzing/monitoring apparatus 600. In the foregoing manner, the passageway for the fluid sampling port 24 may be closer positioned to obtain a carbon dioxide sample from the patient nearer the lungs than known sampling ports which terminate at a proximal end of the endotracheal tube apparatus 20. As shown, secondary passageway 94 also opens into ventilation passageway 80 and is in fluid communication therewith such that a fluid sample may be drawn from the patient by respirator apparatus 500.

Tubing segment 126 in fluid communication with the drug delivery port 26 includes a passageway (lumen) 136 which forms part of the drug delivery passageway which extends through hub connection fitting 70 (as secondary passageway 96) and endotracheal tube 30 (as secondary passageway 46). As shown, the proximal end of tubing segment 126 is connected to a drug delivery port 26, which comprises a drug delivery port connector 146, which may be particularly suited to a drug delivery device 700, such as a syringe (not shown). In certain embodiments, the drug delivery port 26, and more particularly the drug delivery port connector 146 may include a drug aerosolizer as known in the art. As shown, unlike secondary passageway 94, a proximal end of secondary passageway 96 is not in fluid communication with ventilation passageway 80.

Tubing segment 128 in fluid communication with the cuff inflation port 28 includes a passageway (lumen) 138 which forms part of the cuff inflation passageway which extends through hub connection fitting 70 (as secondary passageway 98) and endotracheal tube 30 (as secondary passageway 48). As shown, the proximal end of tubing segment 128 is connected to cuff inflation port 28, which comprises a cuff inflation port connector 148, which connects with a cuff inflation device 800. As shown, unlike secondary passageway 94, a proximal end of secondary passageway 98 is not in fluid communication with ventilation passageway 80. Also unlike the other passageways, the distal end of the cuff inflation passageway is occluded in a known manner and an aperture is formed in a distal end portion of the outer cylindrical side wall 32 to the secondary passageway 48, such that the secondary passageway 48 is in fluid communication with inflation cuff 49 for air to pass through to inflate and deflate the inflation cuff 49.

In the foregoing manner, each of the fluid sampling port 24, drug delivery port 26 and cuff inflation port 28 connect to the endotracheal tube apparatus 20 via the hub connection fitting 70, which remains outside the patient during intubation. As a result, because none of the fluid sampling port 24, drug delivery port 26 and cuff inflation port 28 are located between the endotracheal tube 30 and the person's mouth during use, the tubing segment 124 of fluid sampling port 24, the tubing segment 126 of drug delivery port 26 and the tubing segment 128 of cuff inflation port 28 are not subject to damage during use, such as being severed by the person's teeth in response to a seizure. Also, there is no possibility of the tubing segment 124 of fluid sampling port 24, the tubing segment 126 of drug delivery port 26 or the tubing segment 128 of cuff inflation port 28 are compressed between the person's mouth and the endotracheal tube 30 during use of endotracheal tube apparatus 20 and not operating as intended.

In certain embodiments, tubing segment 124 in fluid communication with the fluid sampling port 24, tubing segment 126 in fluid communication with the drug delivery port 26, and/or tubing segment 128 in fluid communication with the cuff inflation port 28 may be eliminated such that fluid sampling port 24, drug delivery port 26 and cuff inflation port 28 are directly connected to the hub connection body 72 of hub connection fitting 70.

While the medical device 10 disclosed herein is an endotracheal tube apparatus 20, it should be understood that the medical device 10 is not necessarily limited to that of an endotracheal tube apparatus 20, and such may provide uses in minimally invasive surgery, as well as more specific applications such as gastrointestinal and cardiology, and any other use where multi-lumen tube/tubing in combination with the hub connection fitting may be utilized. Furthermore, it should be understood that the multi-lumen tube/tubing and hub connection fitting are not limited to one primary (central) passageway and three secondary passageways, and that any feasible number of passageways may be utilized, such as up to 20 secondary passageways.

Figure 6:
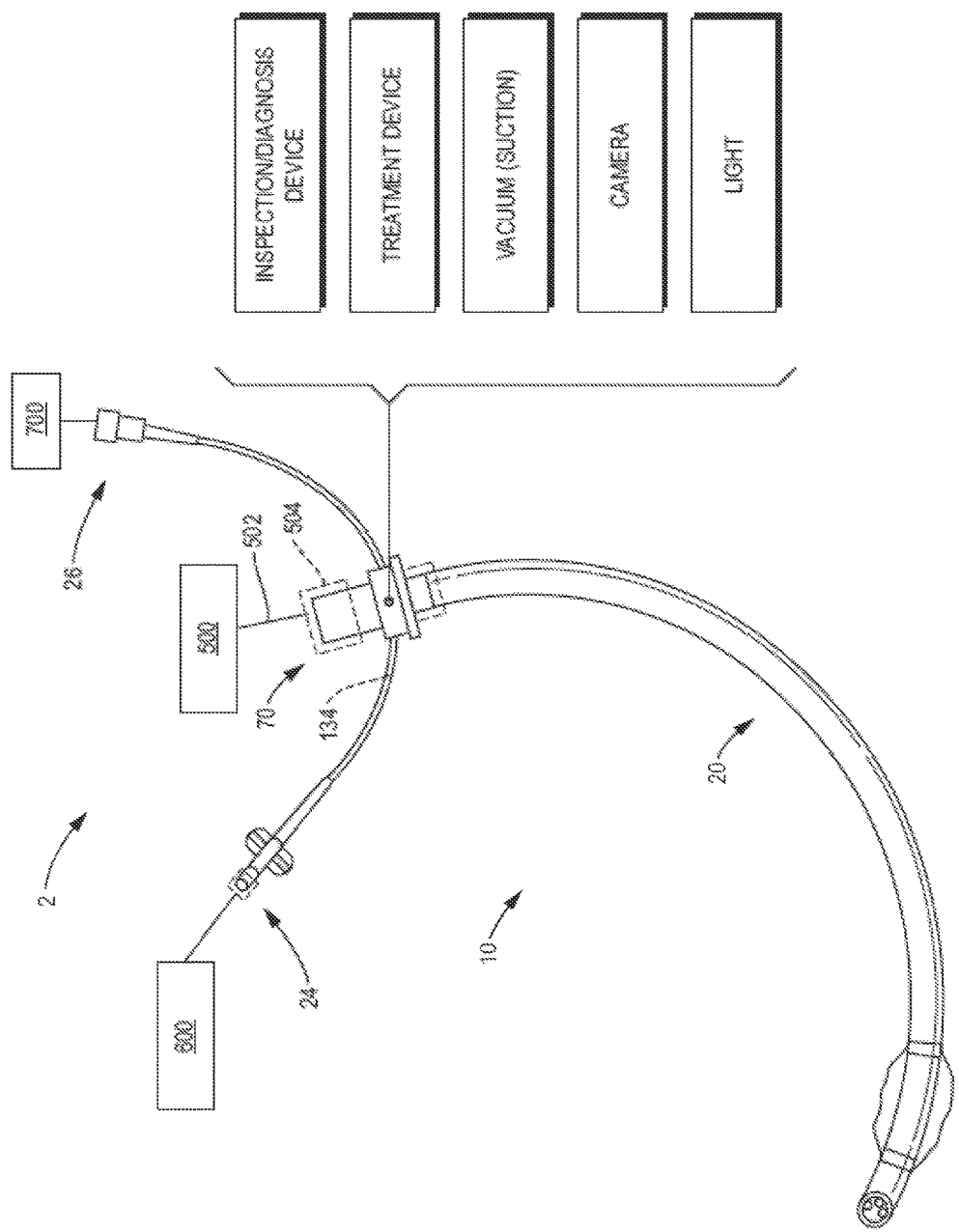
FIG. 6 is a side view of the endotracheal tube apparatus of FIG. 1 including other devices for use therewith.

Referring to FIG. 6, a medical device 10 comprising a tube 30 and a hub connection fitting 70 as disclosed herein may be used for medical inspection, diagnosis and/or treatment where one or more inspection, diagnostic and/or treatment devices are passed through a passageway of the medical device 10. Devices which pass through the passageways may include devices for grasping, suturing, stapling, chemically bonding and/or removal of tissue, and/or for removal of foreign bodies, gas, tissue or liquid sampling; and/or for insertion of inspection/diagnosis devices, treatment devices, a suction device, a camera or other viewing device and/or a light for viewing. A camera may be used for continuous viewing during placement of tube apparatus 20. Devices may include catheters, snares, staplers, and forceps.

Figure 7:
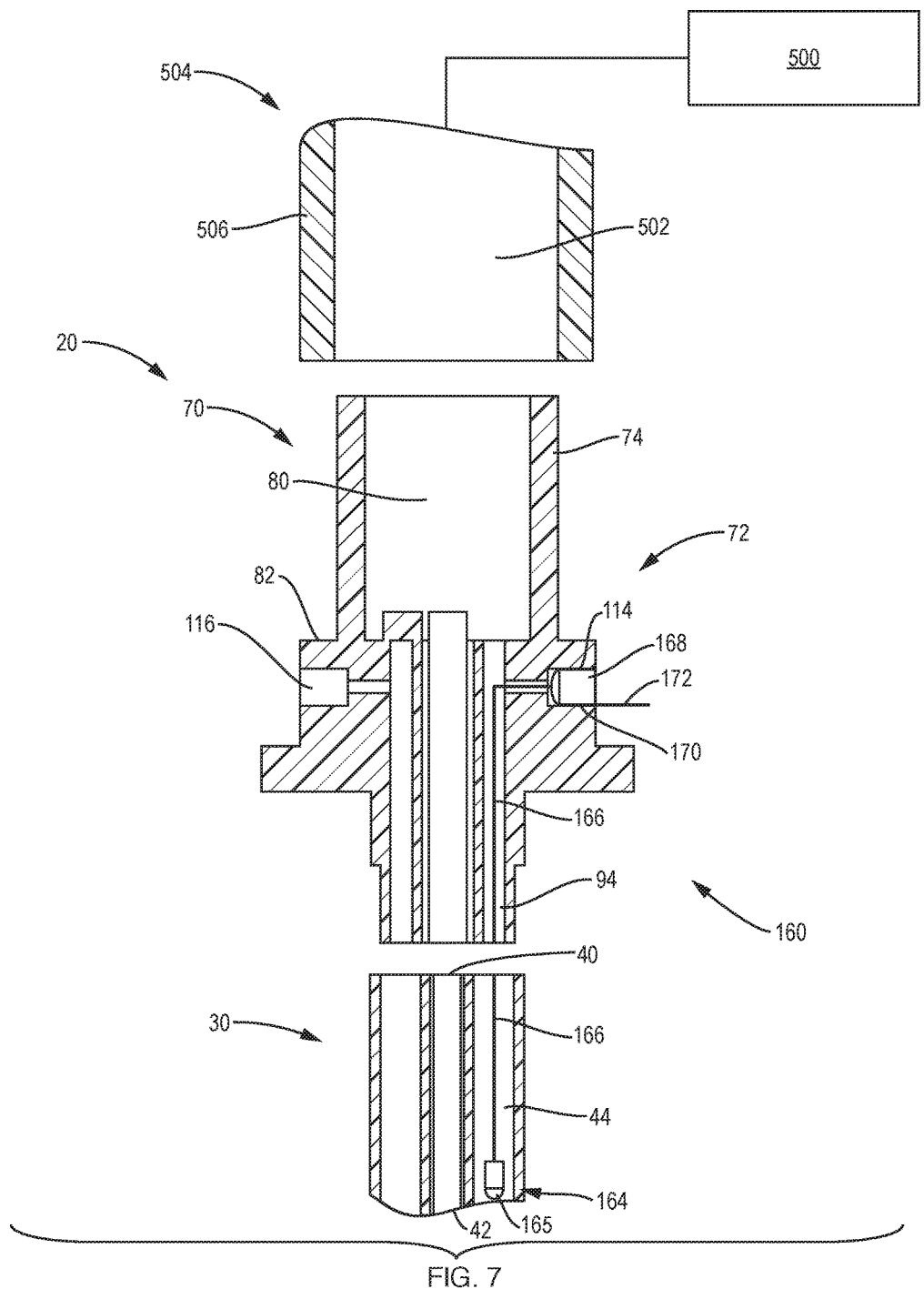
FIG. 7 is an exploded longitudinal cross-sectional side view of another embodiment of the endotracheal tube apparatus.

As shown in FIG. 7, a lighting apparatus 160 may be incorporated in endotracheal tube apparatus 20. As shown, lighting apparatus 160 may comprise a lighting device 164, particularly comprising a light source 165, such as a light-emitting diode (LED), positioned within one of secondary passageways 44, 46 or 48 to emit light from the distal end opening 42 of endotracheal tube 30. The light source 165 may be electrically connectable to a battery 168 by an electrical conductor 166. As shown, battery 168 may be located in one of counter-bores 114, 116, 118 of hub connection fitting 70.

When endotracheal tube apparatus 20 is provided by the manufacturer, the battery 168 may be positioned out of electrical contact with electrical connector 166 to inhibit the lighting apparatus 160 from powering prior to desired use. In other words, the electrical conductors 166 are initially arranged in an open circuit. In such regard, a removable non-conductive liner 170 with a pull tab 172 may be initially positioned between the electrical conductor 166 and the battery 168.

Thereafter, when endotracheal tube apparatus 20 is to be used, the removable non-conductive liner 170 may be removed from hub connection fitting 70 by simply pulling on pull tab 172, which may establish electrical contact between battery 168 and electrical conductor 166 to power the light source 165 of lighting device 164. Alternatively, or in addition to the use of removable non-conductive liner 170, battery 168 may also be pushed further into the counter-bore 114, 116 or 118 to establish electrical contact with electrical conductor 166.

During the insertion of endotracheal tube apparatus 20 into a patient, lighting device 164 may be activated to assist in proper positioning of the endotracheal tube apparatus 20 in the trachea as opposed to the esophagus. In doing so, light emitted from lighting device 164 may be observed through the chest of the patient to further aid in proper positioning.

Light emitted from light source 165 may generally be white (colorless) light, which may be understood as a mixture of all of the wavelengths of the visible spectrum, i.e. the visible portion of the electromagnetic spectrum. White light may also have a correlated color temperature (CCT) of between about 3000 and 8000 K. White light with a CCT of 4000 or less may have a yellowish/reddish color, while white light with a CCT of 8000 K may be bluish in color.

In certain applications, the light emitted from light source 165 may include ultraviolet light, which has a frequency of between 10 nm to 380 nm. More particularly, the ultraviolet light may be UV-C light having a frequency of between 100 nm to 280 nm. The UV-C light emitted from light source 165 may be used for ultraviolet germicidal irradiation (UVGI), which may be understood as a disinfection method which uses short-wavelength ultraviolet (UV-C) light to kill or inactivate microorganisms (e.g. mucus build-up on and/or in the endotracheal tube or other tubing, as well as the patient).

Referring now to FIGS. 8-13, there is shown another embodiment of a medical device 10 comprising a tube apparatus 20, and more particularly an endotracheal tube apparatus 20 of a medical (respiratory) system 2 (see FIG. 1) according to the present disclosure. As with prior embodiments, while a remainder of the disclosure may refer to the tube apparatus as being an endotracheal tube apparatus 20, it should be understood that the present disclosure is not limited to an endotracheal tube apparatus 20, and the present tube apparatus may have other medical applications, as well as non-medical applications, other than that of endotracheal tube apparatus 20.

As with prior embodiments, the endotracheal tube apparatus 20 comprises a flexible, elongated, hollow endotracheal tube 30 and a hub connection fitting 70. Similar to at least one prior embodiment, endotracheal tube apparatus 20 may include a lighting apparatus 160 (see FIG. 12).

Figure 9:
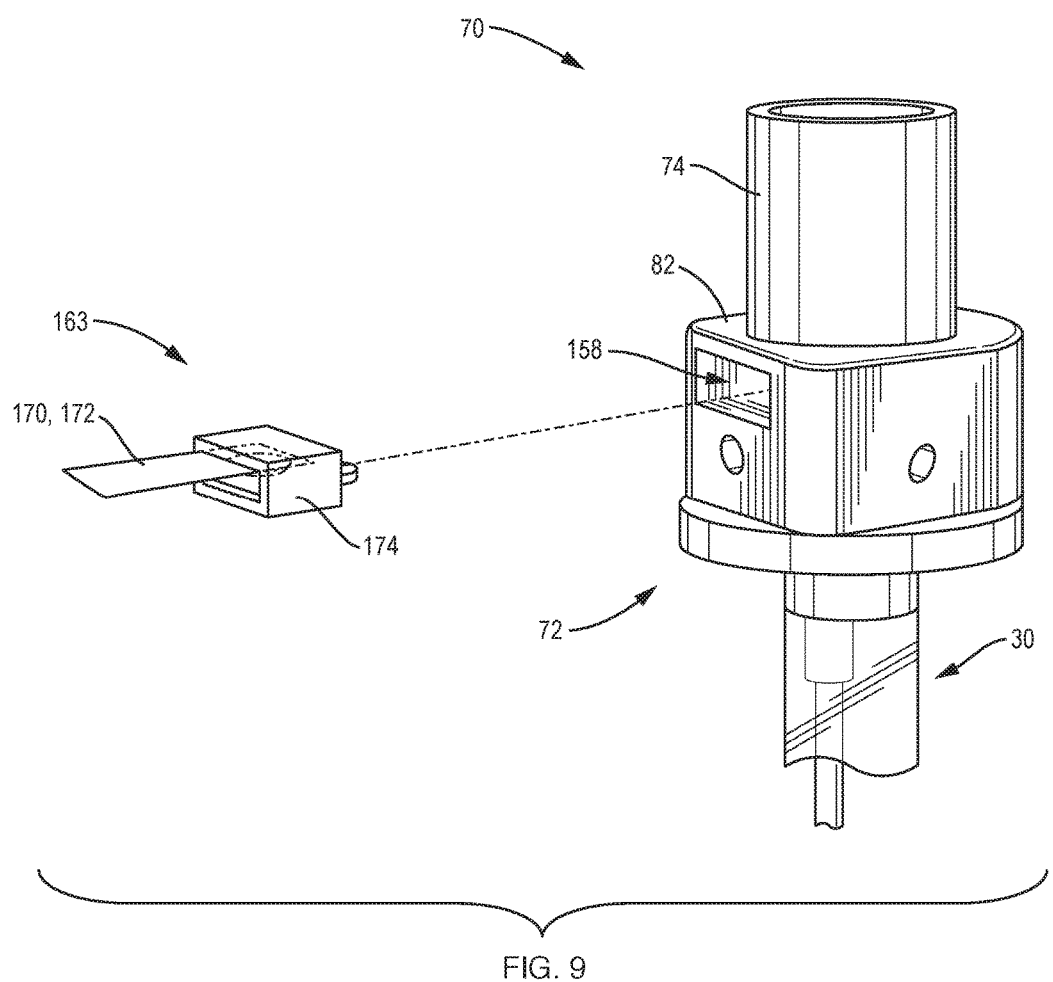
FIG. 9 is an exploded view of a hub connection fitting of the endotracheal tube apparatus of FIG. 8.

Lighting apparatus 160 may comprise a light-emitting device 162, which may include a light-source module 163, coupled with hub connection fitting body 72. As best shown in FIG. 9, light-source module 163 may be insertable into and removable from a light-source module receptacle 158 formed in the hub connection fitting body 72.

Figure 10:
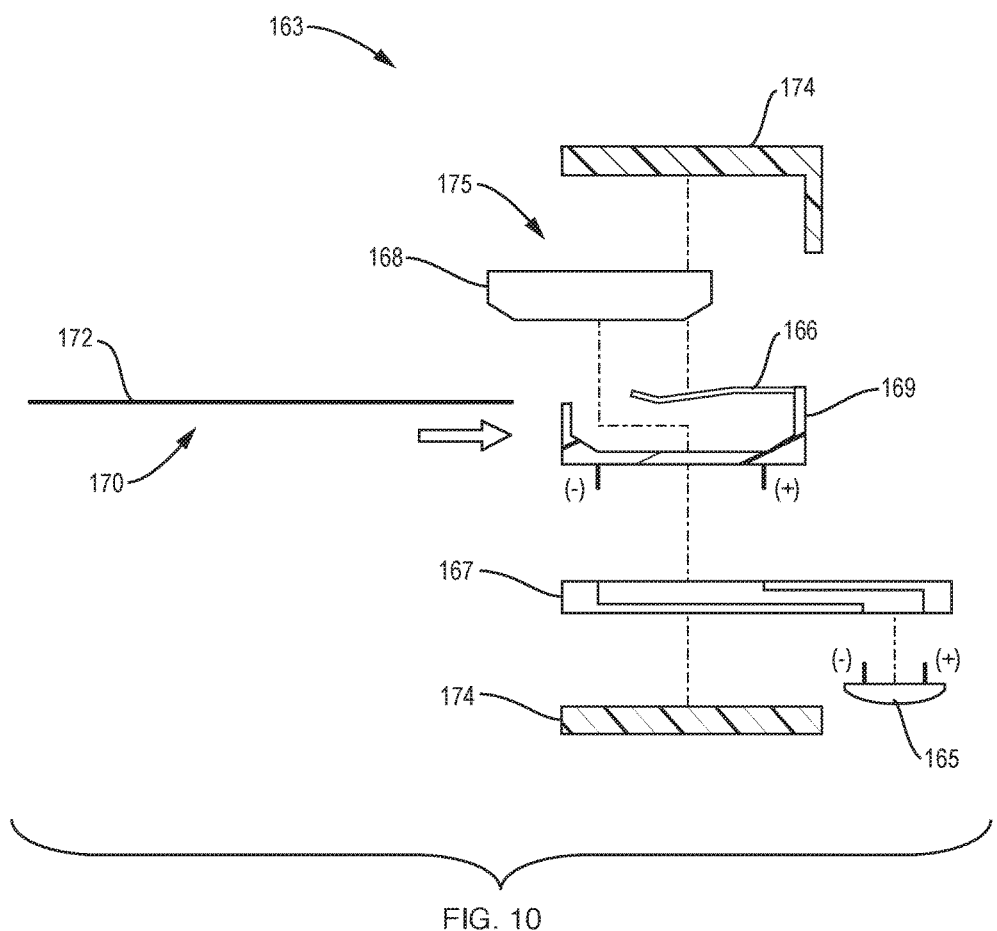
FIG. 10 is an exploded cross-sectional side view of a light source module of the hub connection fitting of the endotracheal tube apparatus of FIG. 8.

As best shown by FIG. 10, light-source module 163 may comprise one or more light sources 165, particularly in the form of a lamp such as one or more light-emitting diodes (LEDs). The LED 165 may be arranged as part of a light engine, which may comprise an LED driver including a printed circuit board (PCB) 167 to which the LED 165 is mounted as well as the electrical wiring/circuitry to control and provide power/signals to the LED 165.

Light-source module 163 may further comprise a housing 174, providing a light-source housing, which forms a cavity 175 to receive the printed circuit board (PCB) 167, as well as power source (battery) 168, battery holder 169 and removable non-conductive liner 170. As shown by FIG. 10, LED 165 and battery holder 169 each provide conductive terminals to electrically couple LED 165 and battery 168, respectively, to printed circuit board 167 to establish an electrical circuit there between.

As with the prior embodiment, when endotracheal tube apparatus 20 is provided by the manufacturer, the battery 168 may be out of electrical communication with LED 165 to inhibit the LED 165 from powering prior to desired use. In such regard, a removable non-conductive liner 170 with a pull tab 172 may be initially positioned between the electrical conductor 166 and the battery 168 to temporarily disconnect the electrical circuit.

Thereafter, when endotracheal tube apparatus 20 is to be used, the removable non-conductive liner 170 may be removed from hub connection fitting 70 by simply pulling on pull tab 172 with a pulling force, which may remove the removable non-conductive liner 170 from hub connection fitting 70 thus establishing electrical contact between battery 168 and electrical conductor 166 to provide power to printed circuit board 167 and LED 165. As such, it should be understood that lighting apparatus 160, and more particularly light-source module 163, makes use of a switchless design with no "on-off switch." More particularly, the lighting apparatus 160 is configured for single use and will continue to operate until power from the battery 168 will no longer provide power to light the LED 165. However, it should be understood that lighting apparatus 160 may also make use of an on-off switch as such switches are known in the art.

Once the light-source module 163 is assembled as shown in FIG. 9, it may be assembled to hub connection fitting body 72 by being inserted into light-source module receptacle 158 formed in the hub connection fitting body 72 by sliding light-source module 163 into light-source module receptacle 158.

In certain embodiments, after a single use of light-source module 163 and the associated power drain of battery 168 upon removal of removable non-conductive liner 170, it may be possible to detachably remove light-source module 163 from hub connection fitting body 72 by sliding the light-source module 163 out of light-source module receptacle 158. Thereafter, battery 168 and removable non-conductive liner 170 may be replaced with a new replacement (charged) battery 168 and a new removable non-conductive liner 170 for reuse of light-source module 163.

In other embodiments, it may be desirable to inhibit removal of light-source module 163 from hub connection fitting body 72 to deter reuse of hub connection fitting 70. In such regard, light-source module 163 and hub connection fitting body 72 may be adhesively bonded to each other, particularly by applying an adhesive (e.g. cyanoacrylate, epoxy) to an exterior surface of the housing 174 to be in contact with the hub connection fitting body 72 prior to inserting the light-source module 163 into light-source module receptacle 158. Thereafter, before the adhesive sets (e.g. cures and/or cools), the light-source module 163 may be slid into light-source module receptacle 158 after which time the adhesive may set. Alternatively, or in addition to the use of a separate adhesive, once the light-source module 163 is slid into light-source module receptacle 158, the housing 174 and the hub connection fitting body 72 may be welded together, such as by vibration welding or ultrasonic welding in a known manner, for a more permanent assembly.

Figure 11:
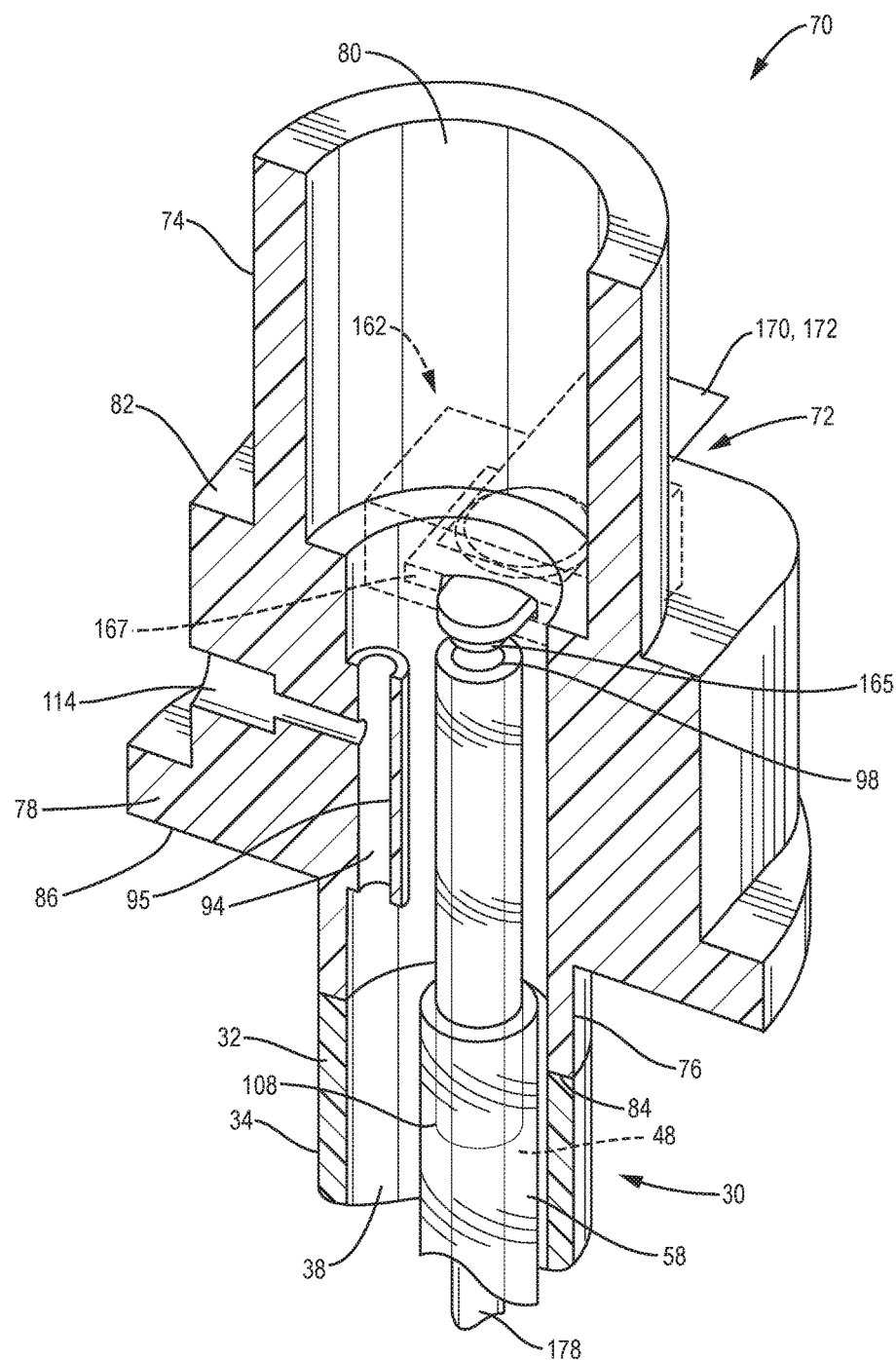
FIG. 11 is longitudinal cross-sectional perspective view of the endotracheal tube apparatus of FIG. 8.
Figure 12:
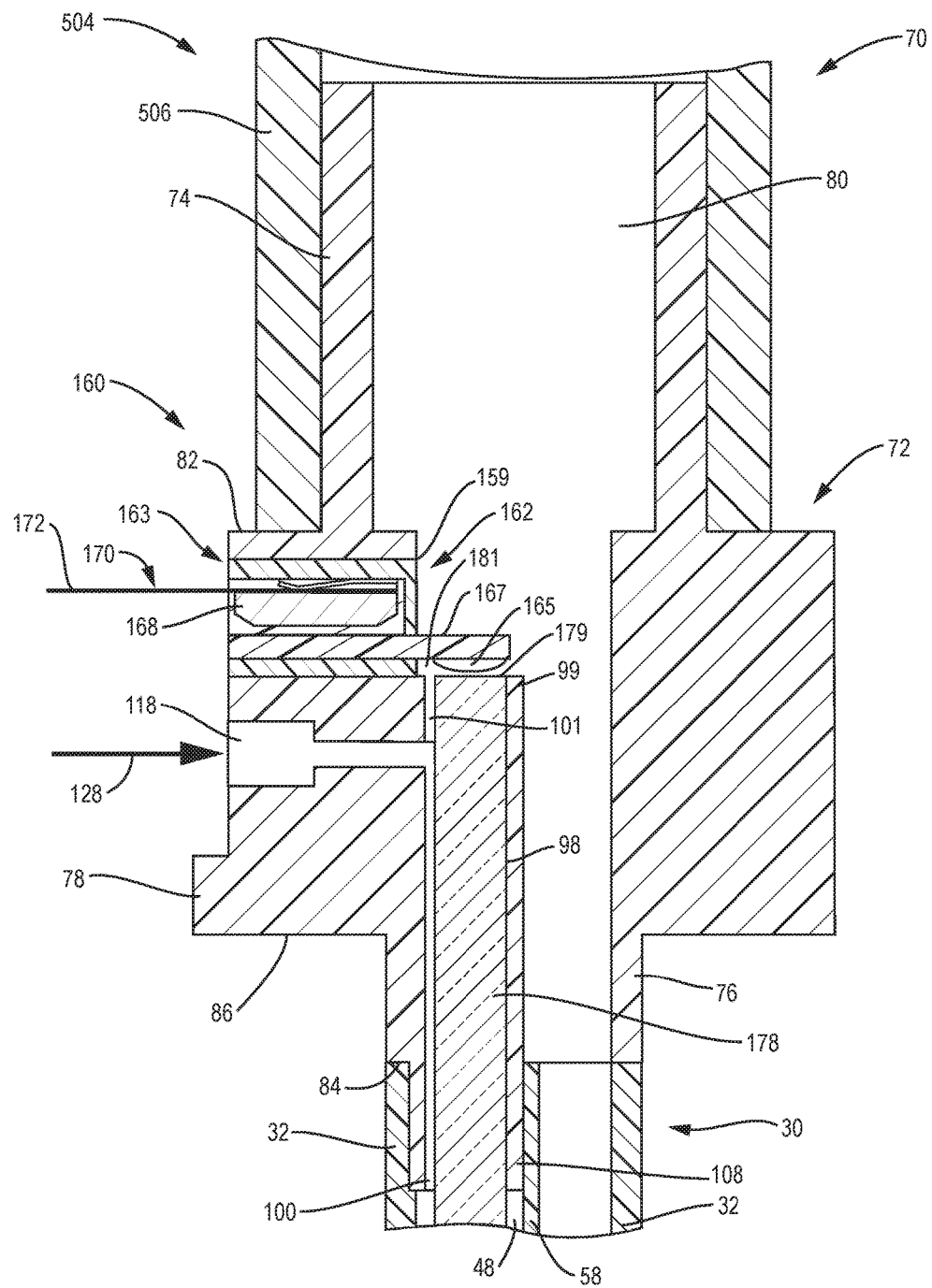
FIG. 12 is a first longitudinal cross-sectional side view of the endotracheal tube apparatus of FIG. 8.
Figure 13:
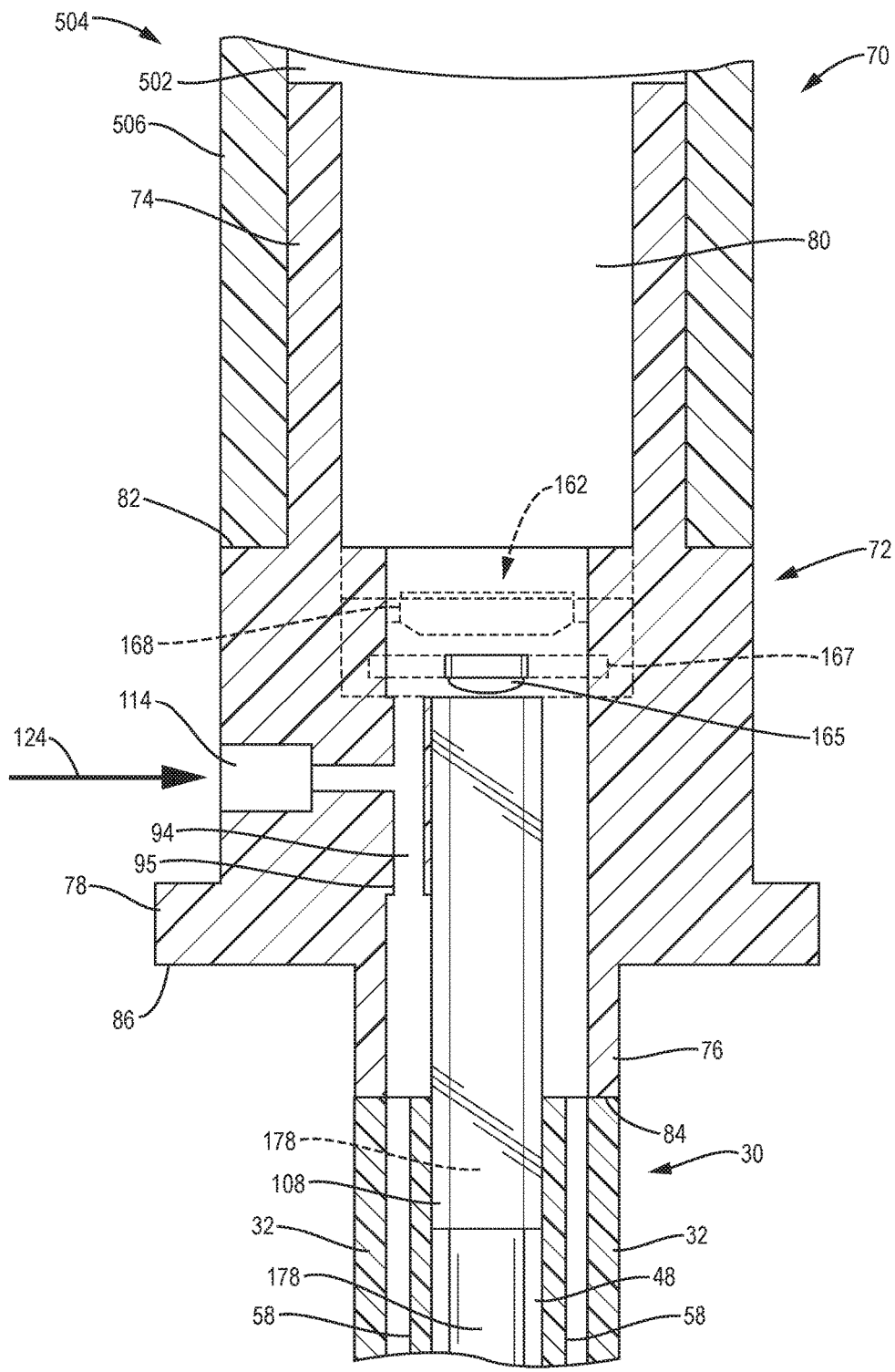
FIG. 13 is a second longitudinal cross-sectional side view of the endotracheal tube apparatus of FIG. 8.

Referring now to FIGS. 11-13, there are shown various views of the light-source module 163 coupled with hub connection fitting body 72. As shown, when properly seated in light-source module receptacle 158, the LED 165 and the portion of the printed circuit board 167 to which LED 165 is mounted may enter into ventilation passageway 80 of hub connection fitting body 72, particularly through a aperture 159 located at inner end of the light-source module receptacle 158. As shown, LED 165 is arranged to direct light down the longitudinal length of the endotracheal tube 30 along the longitudinal axis, while the thickness of the printed circuit board 167 and the battery 168 are arranged transverse to the longitudinal axis.

In order to provide increased light emittance at the distal end of tube apparatus 20, lighting apparatus 160, and more particularly, light-emitting device 162 may further comprise a tubular light guide 178 (which may also be referred to as a light tube or pipe) which extends along the length of endotracheal tube 30. As shown, the proximal end 179 of the tubular light guide 178 may be adjacent (or in contact) and aligned with the LED 165 such that the LED 165 overlies the proximal end 179 of the tubular light guide 178 and is optically coupled therewith. As shown, a narrow gap 181, e.g. 0.1 mm to 3 mm, may exist between the LED 165 and the proximal end 179 of the tubular light guide 178.

Tubular light guide 178 may be formed of a bendable, light transmissive (e.g. substantially transparent) cylinder of extruded thermoplastic polymer (e.g. polycarbonate) or glass. Tubular light guide 178 may comprise a fiber optic cable having a single elongated optical fiber or a plurality of elongated optical fibers (i.e. a multi-fiber fiber optic cable). Tubular light guide 178 may be a solid cylinder, which may contain and transmit light by total internal reflection, or a hollow cylinder which may contain and transmit light along a reflective lining. As shown, tubular light guide 178 is a solid, cylindrical elongated optical fiber, particularly formed of glass, which may have a diameter in a range of 0.1 mm to 2 mm (including all ranges and increments there between) and more particularly in a range of 0.4 mm to 1.1 mm (including all ranges and increments there between).

Tubular light guide 178 may be located within one of secondary passageways 44, 46 or 48 to emit light at or adjacent the distal end opening 42 of endotracheal tube 30. As shown, tubular light guide 178 is arranged in secondary passageway 98 of hub connection fitting which is in fluid communication with secondary passageway 48 of endotracheal tube 30.

As set forth herein, secondary passageways 98 and 48 define a portion of the cuff inflation passageway in fluid communication with cuff inflation port 28 and inflation cuff 49. In the foregoing manner, air pressure to inflate inflation cuff 49 and light to illuminate the distal end of the endotracheal tube 30 may be extended through a single secondary passageway of hub connection fitting body 72 and endotracheal tube 30 to reduce the overall number of secondary passageways. While the passageway for the drug delivery port 26 is not shown, such has been eliminated from the drawing to reduce complexity.

As set forth above, with regards to assembly, the distal end of secondary passageway 98 is defined by a male connector portion 108 of the hub connection fitting body 72 which is dimensioned to be inserted into secondary passageway 48 of endotracheal tube 30 and interference (frictionally) fit with the inside diameter of the side wall 58, while the proximal end of the endotracheal tube 30 is to contact and butt against annular lip/shoulder 84 of distal body portion 76. Further, an annular ring 90 (see FIG. 2A) may overlie distal body portion 76 as described above.

Tubular light guide 178 may be inserted into secondary passageways 98 and 48 of the hub connection fitting body 72 and endotracheal tube 30, respectively, before or after the hub connection fitting body 72 and endotracheal tube 30 are assembled. As shown, tubular light guide 178 may have an outer diameter which is less than or substantially equal (i.e. within manufacturing tolerance) to the inner diameter of secondary passageway 98.

In order to seal a proximal end of the secondary passageway 98 against air leaks (in the case where air pressure to inflate inflation cuff 49 and light to light the distal end of the endotracheal tube 30 extend through the same secondary passageway of hub connection fitting 70 and endotracheal tube 30), the gap 181 between the LED 165 and the proximal end of secondary passageway 98 and tubular light guide 178 may be filled with an light transmissive (e.g. substantially transparent) sealing composition 101, such as a polymer, adhesive or potting resin. In addition, or alternative, the polymer may be located between the inside diameter of secondary passageway 98 and the outside diameter of the tubular light guide 178 adjacent the proximal end thereof (above/proximal to counter-bore 118) to adhesively bond the tubular light guide 178 to the side wall 99 of secondary passageway 98.

Where tubular light guide 178 has an outer diameter substantially equal to the inner diameter of secondary passageway 98, the secondary passageway 98 of hub connection fitting 70 may include a semi-circular notch 100 to facilitate the passage of air through secondary passageway 98. Similar to above, the proximal end of the notch 100 of hub connection fitting 70 may be filled with a sealing composition 101, which may comprise a polymer, adhesive or potting resin, to inhibit air leaks and/or adhesively bond the tubular light guide 178 to the side wall 99 of secondary passageway 98 of hub connection fitting 70. Notch 100 may also be formed within secondary passageway 48 during extrusion of endotracheal tube 30 if so formed by extrusion.

At the distal end of endotracheal tube 30, secondary passageway 48 of endotracheal tube 30 may be sealed distal to air inlet/outlet opening 50 (see FIG. 8) with a plug 182 of light transmissive (e.g. substantially transparent) polymer material. The plug 182 may be formed separate from the endotracheal tube 30 or formed as one-piece therewith. In the event of being formed in one piece, a distal end region of the endotracheal tube 30 may be heated and formed into the ventilation passageway 38 to close the ventilation passageway 38 and provide the plug 182. The distal end 180 of tubular light guide 178 may terminate within secondary passageway 48 adjacent the plug 182, e.g. less than 3 mm, so the tubular light guide may slide in secondary passageways 98, 48 in a range of 0.5 mm to 6 mm (including all ranges and increments there between) and more particularly in a range of 1 mm to 4 mm) including all ranges and increments there between) as explained below.

If tubular light guide 178 is made bendable, albeit also breakable, material, such as if formed of a glass optical fiber, then it may be desirable to design the tubular light guide 178 shorter than the overall length of the secondary passageway 98, 48 in which it resides as set forth above, and merely insert the tubular light guide 178 in secondary passageways 98, 48 such that the tubular light guide 178 may slide freely therein. In such case, the tubular light guide 178 may not be bonded to the side wall 99 or 58 of either secondary passageway 98 or 48, respectively, but be retained in the secondary passageway 98, 48 by the LED 165 at the proximal end of the secondary passageway 98 (or sealing composition 101) and the plug 182 at the distal end of the secondary passageway 48. As a result, the tubular light guide 178 may be less opt to break when endotracheal tube 30 undergoes bending. In the event it becomes desirable to bond the tubular light guide 178 to the side wall 99 and/or 58 of either secondary passageway 98 or 48, respectively, the tubular light guide 178 should not be bonded at more than one fixed point, again to inhibit the likelihood of breaking when endotracheal tube 30 undergoes bending.

Figure 8:
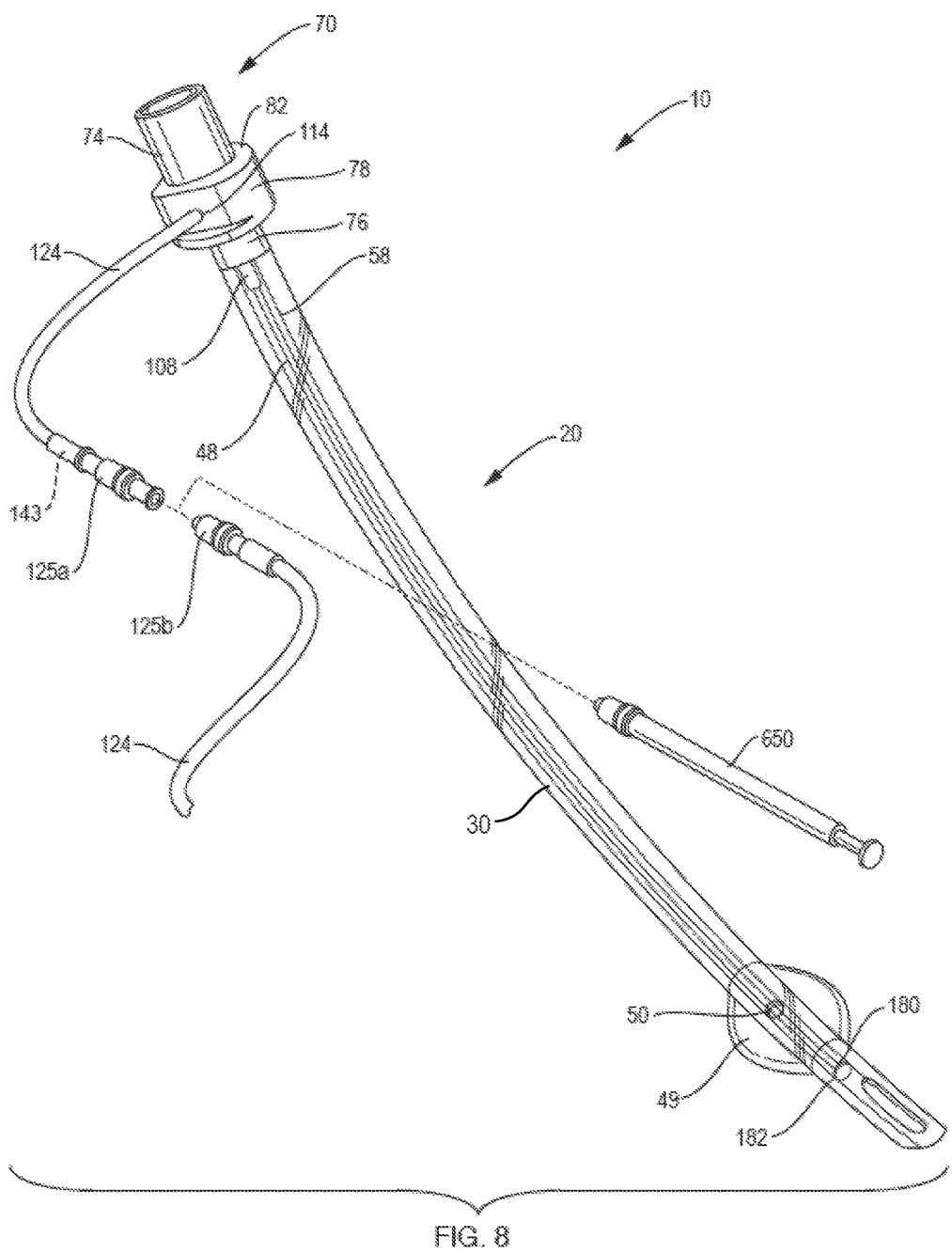
FIG. 8 is a perspective view of another embodiment of the endotracheal tube apparatus.
Figure 13A:
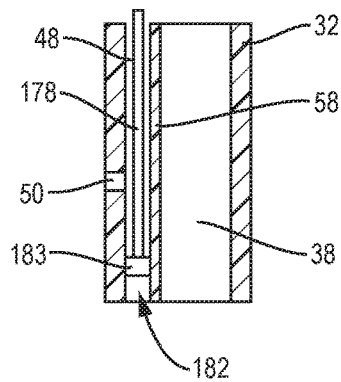
FIG. 13A is a longitudinal cross-sectional side view of a distal end region of another embodiment of the endotracheal tube apparatus.
Figure 13B:
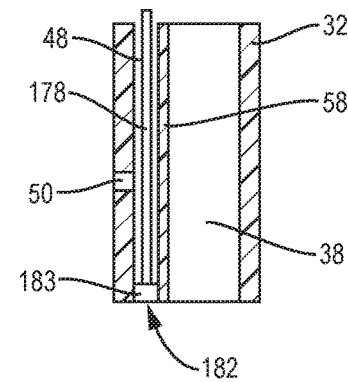
FIG. 13B is a longitudinal cross-sectional side view of a distal end region of another embodiment of the endotracheal tube apparatus.
Figure 13C:
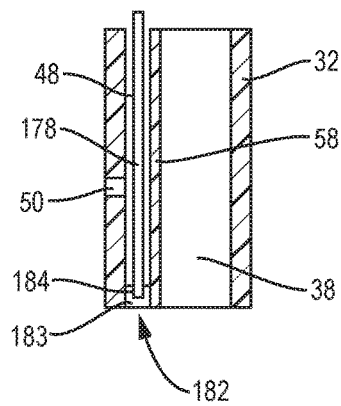
FIG. 13C is a longitudinal cross-sectional side view of a distal end region of another embodiment of the endotracheal tube apparatus.
Figure 13D:
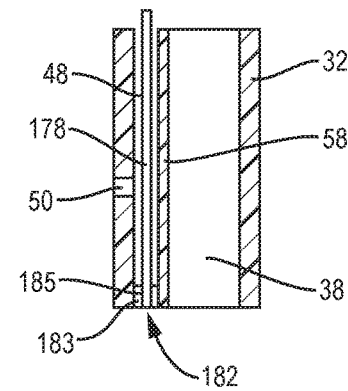
FIG. 13D is a longitudinal cross-sectional side view of a distal end region of another embodiment of the endotracheal tube apparatus.
Figure 13E:
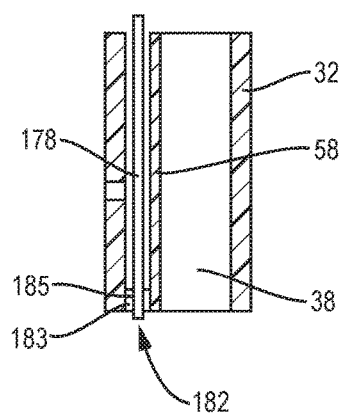
FIG. 13E is a longitudinal cross-sectional side view of a distal end region of another embodiment of the endotracheal tube apparatus.
Figure 13F:
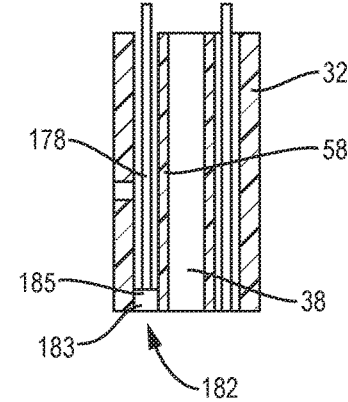
FIG. 13F is a longitudinal cross-sectional side view of a distal end region of another embodiment of the endotracheal tube apparatus.

Referring to FIGS. 13A-13F, there are shown other embodiments of plug 182 of FIG. 8. As shown in FIG. 13A, similar to FIG. 8, the plug body 183 of plug 182 is recessed from the distal end 33 of the endotracheal tube 30. In FIG. 13B, the plug 182 is moved distally such that the plug body 183 is located at the distal end 33 of the endotracheal tube. In FIG. 13C, the plug body 183 may have a blind recess 184 therein to receive tubular light guide 178. If tubular light guide 178 is to be connected to the plug body 183, such may provide with an interference therewith, or sealing composition 101 being placed therein. In FIG. 13D, rather than having a blind recess 184, plug body 183 may include a through-hole 185 which extends completely through plug body 183. In such regards, the distal end 180 of tubular light guide 178 may be located at the distal end 33 of the endotracheal tube. In FIG. 13E, rather than the distal end 180 of tubular light guide 178 being recessed or at (parallel with) the distal end 33 of the endotracheal tube 30, the distal end 180 of tubular light guide 178 may extend beyond the distal end 33 of the endotracheal tube 30 (e.g. by 1 mm). In FIG. 13F, in another embodiment, the endotracheal tube 30 is shown to have a plurality of tubular light guides 178, with the light guide 178 on the left having a plug 182 adjacent the distal end 180 thereof, and the light guide 178 on the right not having a plug 182. Both light guides 178 may be used to emit light, or alternatively be used as temperature sensors (e.g. contact thermometer) as disclosed elsewhere herein to measure core body temperature, particularly during therapeutic hypothermia treatment.

Returning to FIG. 13, the present embodiment also includes a counter-bore 114 to receive the distal end portion of tubing segment 124 in fluid communication with the fluid sampling port 24. However, in contrast to the previous embodiment, the secondary passageway 94 defined by side wall 95 has been shortened to eliminate male connector portion 104, particularly as the corresponding secondary passageway 44 in endotracheal tube 30 has been eliminated. Alternatively, side wall 95 may be completely eliminated such that only the counterbore 114 remains.

Similar to the fluid sampling port 24, the secondary passageway 96 defined by sidewall 97 may be shortened to eliminate male connector portion 106. Alternatively, side wall 97 may be completely eliminated such that only the counterbore 116 remains.

Referring briefly to FIGS. 1 and 8, as shown, prior to the fluid sampling port threaded connector 144 (which connects fluid sampling port 24 to the analyzing/monitoring apparatus 600), tubing segment 124 may include a connectable and disconnectable mating first and second connectors 125a, 125b. Connectors 125a, 125b may more particularly include a one-way valve, which only allow exhaled gas(es) from the patient within tubing segment 124 to travel towards analyzing/monitoring apparatus 600. Further, first connector 125a may close the valve and passageway 134 in the event of disconnection.

During use of fluid sampling port 24, in the event passageway 134 prior to first connector 125 becomes clogged with mucus, saliva or other secretions, the first and second connectors 125a, 125b may be disconnected from one another without a change in pressure (positive or negative) within ventilation passageway 38. Thereafter, a syringe 650 may be connected to first fastener 125a to reopen the one-way valve and inject air into passageway 134 to remove the secretions therein by forcing them back to the ventilation passageway 38. Thereafter, the syringe 650 may be disconnected from first fastener 125a, and first fastener 125a may be reconnected with second fastener 125b.

Figure 14:
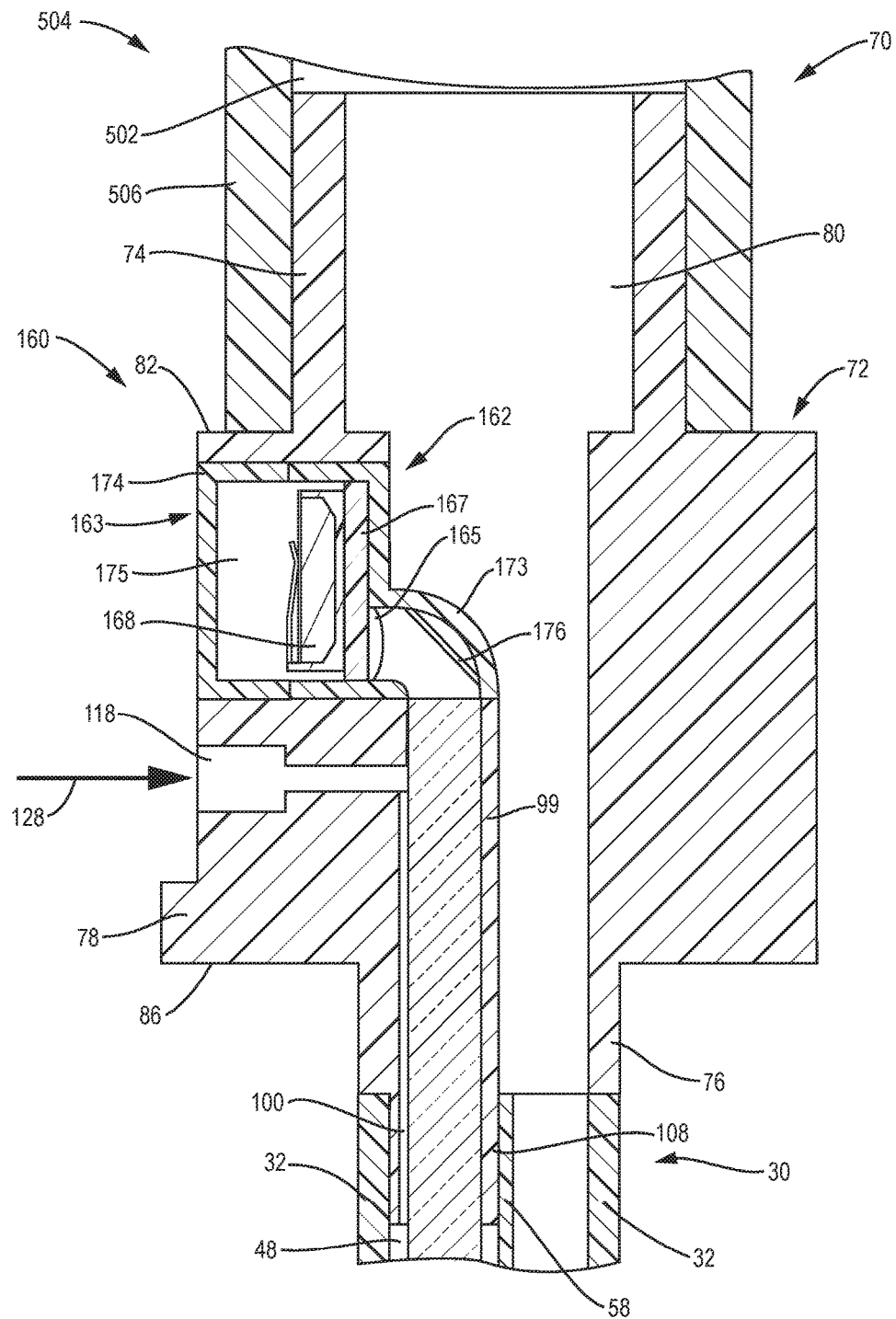
FIG. 14 is a longitudinal cross-sectional side view of another embodiment of the endotracheal tube apparatus.

Referring now to FIG. 14, there is shown another embodiment of medical device 10 comprising a tube apparatus 20, and more particularly an endotracheal tube apparatus 20 of a medical (respiratory) system 2 according to the present disclosure. In contrast to the prior embodiment, when properly seated in light-source module receptacle 158, the LED 165 and the portion of the printed circuit board 167 to which LED 165 is mounted do not enter into ventilation passageway 80 of hub connection fitting body 72. As shown, LED 165 is arranged to direct light transverse to the longitudinal length of ventilation passageway 80 and transverse to the longitudinal axis, while the thickness of the printed circuit board 167 and the battery 168 are arranged parallel to the longitudinal axis.

In order for light from LED 165 to be directed down the longitudinal length of ventilation passageway 80 along the longitudinal axis, housing 174 may include a 90 degree elbow 173 having a light reflective surface 176 to redirect light from LED 165 approximately 90 degrees such the light from LED 165 is directed down the longitudinal length of secondary passageways 48, 98 along the longitudinal axis.

In addition to redirecting light from LED 165, elbow 173 also may seal against cylindrical side wall 99 defining secondary passageway 98. In such manner, the gap 181 between the LED 165 and the proximal end of secondary passageway 98 and tubular light guide 178 of the prior embodiment is also eliminated, along with the potential need to seal the proximal end of the secondary passageway 98 against air leaks.

As may be understood from the foregoing embodiments, the tube apparatus 20, such as an endotracheal tube apparatus, may incorporate a lighting apparatus 160 to provide visual aid during endotracheal intubation to better ensure proper placement of the endotracheal tube in the trachea.

Figure 15:
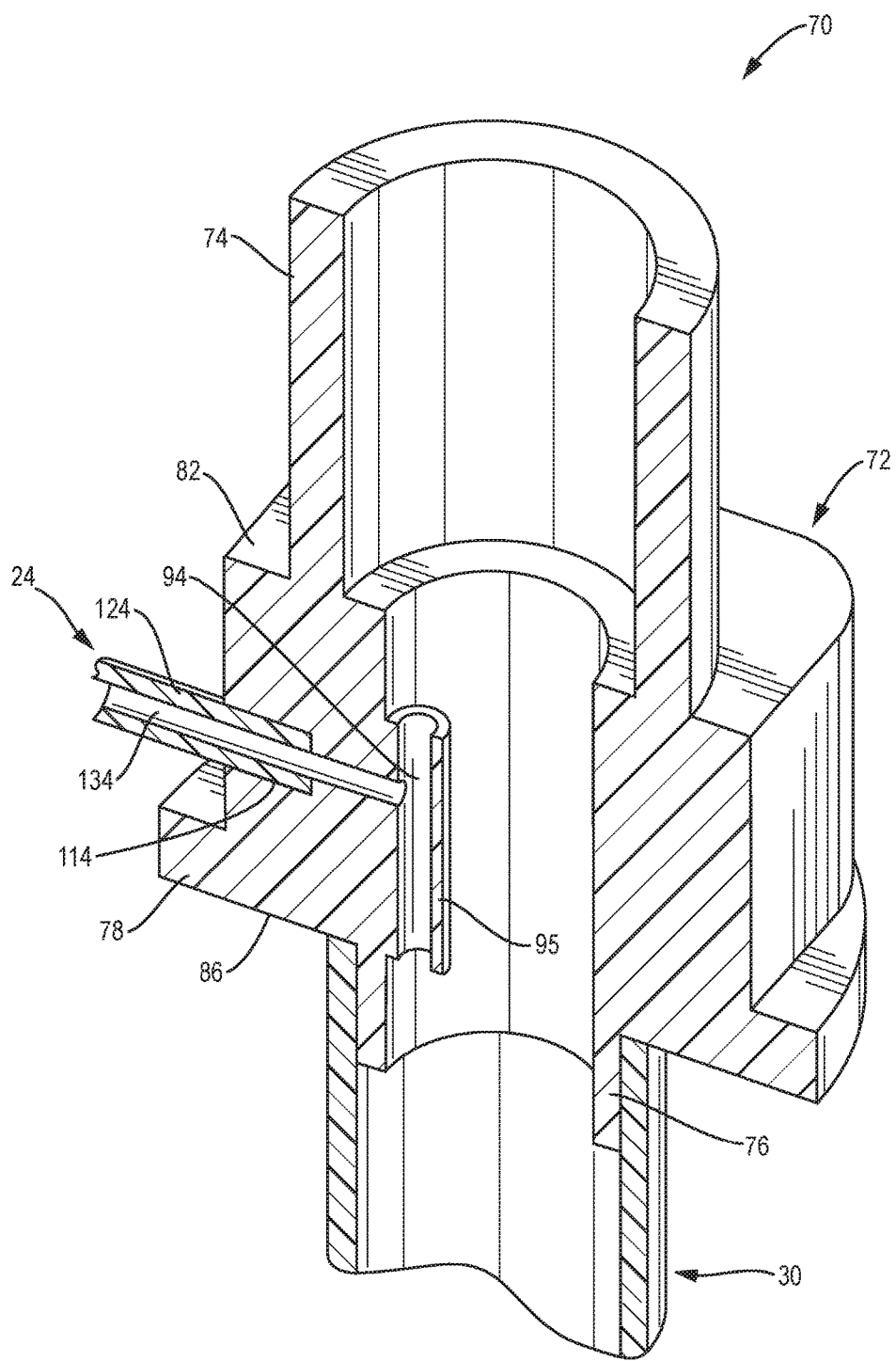
FIG. 15 is a longitudinal cross-sectional side view of another embodiment of the endotracheal tube apparatus.

Referring now to FIG. 15, there is shown another embodiment of medical device 10 comprising a tube apparatus 20, and more particularly an endotracheal tube apparatus 20 of a medical (respiratory) system 2 according to the present disclosure. As shown, the light-emitting device 162 has been completely eliminated. Furthermore, rather than forming a butt joint between distal body portion 76 and endotracheal tube 30, a lap joint is shown such that the inner diameter of the proximal end portion of endotracheal tube 30 overlaps and forms an interference fit with the outer diameter of the distal body portion 76 of hub connection fitting 70 and butts up against annual lip/shoulder 86.

With the tube apparatus 20 of FIG. 15, the outer diameter of distal body portion 76 may be changed, particularly through modifying the injection mold tooling. As such, hub connection fittings 70 may be made with the outer diameter of distal body portion 76 having differing diameters. In such fashion, the various outer diameters of distal body portion 76 may be used to form the overlap joint with an interference fit to endotracheal tubes 30 or other tubes 30 with varying inner diameters.

Figure 16:
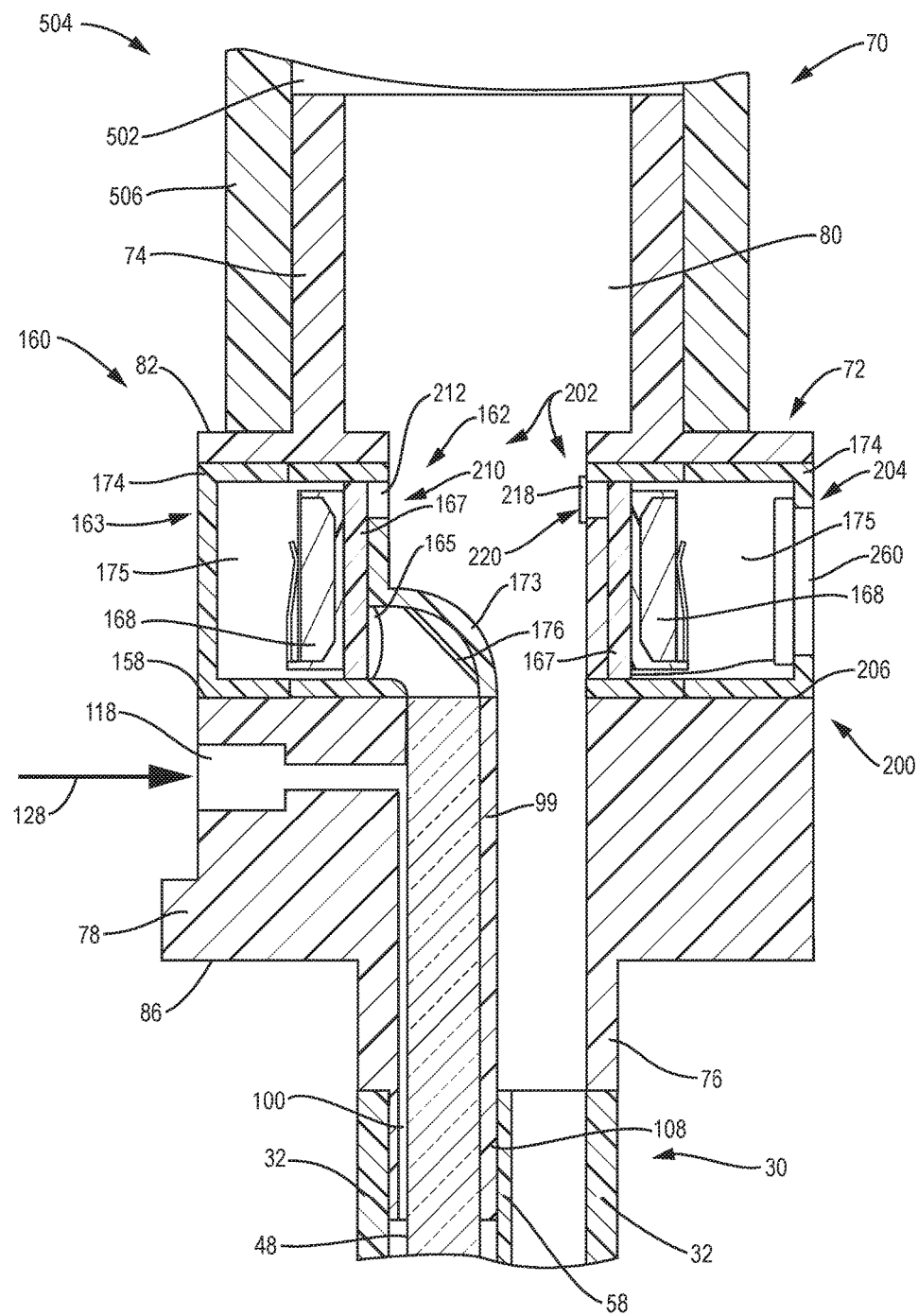
FIG. 16 is a longitudinal cross-sectional side view of another embodiment of the endotracheal tube apparatus.
Figure 17:
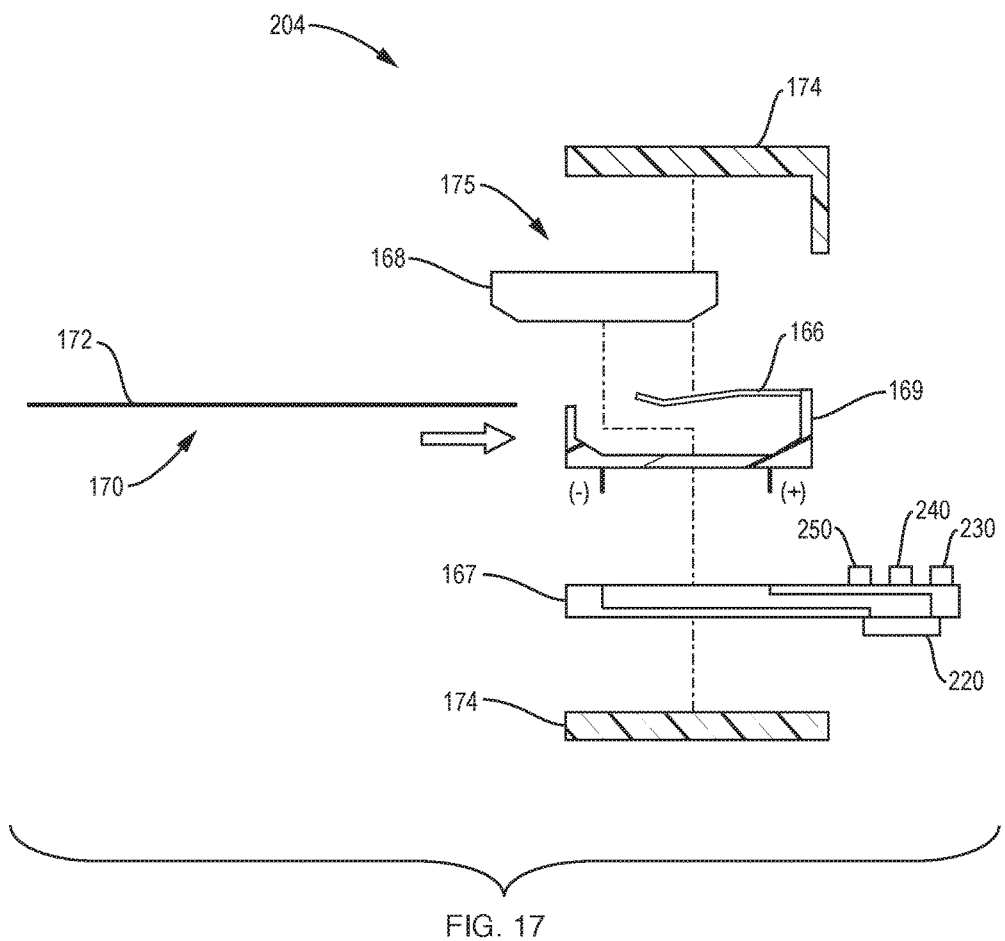
FIG. 17 is an exploded cross-sectional side view of a sensor module of the hub connection fitting of the endotracheal tube apparatus of FIG. 16.

Referring now to FIGS. 16-17, there is shown another embodiment of a medical device 10 comprising a tube apparatus 20, and more particularly an endotracheal tube apparatus 20 of a medical (respiratory) system 2 (see FIG. 1) according to the present disclosure. As with prior embodiments, while a remainder of the disclosure may refer to the tube apparatus as being an endotracheal tube apparatus 20, it should be understood that the present disclosure is not limited to an endotracheal tube apparatus 20, and the present tube apparatus may have other medical applications, as well as non-medical applications, other than that of endotracheal tube apparatus 20.

As with prior embodiments, the endotracheal tube apparatus 20 comprises a flexible, elongated, hollow endotracheal tube 30 and a hub connection fitting 70. Similar to at least one prior embodiment, endotracheal tube apparatus 20 may include a lighting apparatus 160 (see FIG. 12).

Endotracheal tube apparatus 20 may further comprise a sensor apparatus 200, such as a gas sensor apparatus arranged to detect one or more respiration gases exhaled by a patient. More particularly, the sensor apparatus 200 may be arranged to detect the existence or non-existence of at least one particular gas within the composition of respiration gases exhaled by a patient. Even more particularly, sensor apparatus 200 may be arranged to detect a level of at least one particular gas within the composition of respiration gas exhaled by a patient (e.g. detect carbon dioxide gas). In such a manner, sensor apparatus 200 then may determine whether the level of the particular gas being exhaled by the patient is below or above values which are generally recognized as being normal for purposes of determining further treatment.

As shown, sensor apparatus 200 may comprise at least one sensor 202, which may be provided by one or more sensor modules 204 coupled within hub connection fitting body 72. Sensor module 204 may be insertable and removable into a sensor module receptacle 206 formed in the hub connection fitting body 72.

Sensor 202 may be configured to detect one or more respiration gases exhaled by the patient, particularly carbon dioxide. As explained in greater detail below, sensor 202 may be a carbon dioxide sensor, such as particularly used for non-diverging capnography.

Capnography may be understood as the monitoring of the concentration or partial pressure of carbon dioxide gas in a patient's respiratory gases. Carbon dioxide monitoring may be performed using either diverting or non-diverting sampling, which may alternatively be referred to as sidestream or mainstream sampling, respectively. With use of diverting or sidestream capnography, a portion of a patient's respirated gases are transported from the sampling site through sampling tubing to a carbon dioxide sensor in a capnograph (which may also be referred to as a capnometer) as set forth with the foregoing embodiments. Alternatively, with use of non-diverting or mainstream capnography, the patient's respirated gases are analyzed at the sampling site by the carbon dioxide sensor, rather than being transported from the sampling site through sampling tubing to carbon dioxide sensor in the capnograph. Stated another way, the difference between mainstream (non-diverting) capnography and sidestream (diverting) capnography may be understood as measuring carbon dioxide at the sampling site (in the endotracheal apparatus) versus measuring carbon dioxide at a monitor location remote from the sampling site. Because non-diverting capnography measures carbon dioxide at or closer to the sampling site, the data is closer to real time.

As set forth above, sensor 202 may be a carbon dioxide sensor. More particularly, sensor 202 may be a spectroscopic sensor and more particularly an infrared gas sensor, such as a nondispersive infrared sensor, given that carbon dioxide absorbs infrared radiation. In general operation, a beam of infrared light passed across the gas sample falls on the infrared sensor. The presence of carbon dioxide in the gas leads to a reduction in the amount of light falling on the sensor, which changes the voltage output in a circuit. Thus, it may be understood that when no carbon dioxide is in the expired gases of a patient, the voltage level would be at its highest, and when a maximum level of carbon dioxide is in the expired gases of a patient, the voltage level would be at its lowest. The voltage change over time may then be converted using an algorithm to an output graph of expiratory carbon dioxide which may be measured in millimeters of mercury ("mmHg") plotted against time, or, less commonly, but more usefully, expired volumetric concentration of carbon dioxide. Thus, the light intensity is detected and may be converted into a voltage signal which is correlated to a gas concentration value by the algorithm.

As such, sensor 202 may further comprise an infrared emitter 210 and an infrared detector 220. An interference filter 218 may be located in front of the infrared detector 220 to prevent wavelengths other than that specific to the measured gas from passing through to the detector. Alternatively, or in addition to, the window of the infrared detector 220 maybe coated with sapphire to avoid condensation thereon which could adversely affect readings. Infrared emitter 210 and infrared detector 220 may be aligned on opposing sides of the ventilation passageway 80 such that infrared light emitted from infrared emitter 210 is detected by infrared detector 220.

Infrared emitter 210 may comprise one or more infrared light sources 212 particularly in the form of a lamp such as one or more infrared light-emitting diodes (LEDs). Infrared LED 212 may be part of light-source module 163 if such is included with the particular embodiment of medical device 10, in which case light-source module may double as a combined sensor module.

Similar to LED 165, LED 212 may be arranged as part of a light engine, which may comprise an LED driver including a printed circuit board (PCB) 167 to which the LED 212 is mounted as well as the electrical wiring/circuitry to control and provide power/signals to the LED 212. Also similar to LED 165, LED 212 may receive power from power source (battery) 168 held in battery holder 169 and be activated with the removal of removable non-conductive liner 170. Power source 168 may also be used to heat the infrared emitter 210 and an infrared detector 220, such as by use of a resistor located adjacent thereto to prevent or reduce condensation.

In alternative embodiments, if light-source module 163 is not included with the medical device 10, then light-source module 163 may particularly function solely as a sensor module with the operation of infrared emitter 210.

Similar to module 163, sensor module 204 may include a housing 174, which forms a cavity 175 to receive the printed circuit board (PCB) 167, as well as power source (battery) 168, battery holder 169 and removable non-conductive liner 170. As shown by FIG. 17, battery holder 169 may provide conductive terminals to electrically couple battery 168 to printed circuit board 167 and infrared detector 220 to establish an electrical circuit there between. With the foregoing arrangement, infrared detector 220 may be powered for use by battery 168.

Infrared detector 220 is arranged to detect infrared light from infrared light source 212 of infrared emitter 210. As set forth above, presence of carbon dioxide in the gas leads to a reduction in the amount of light falling on the infrared detector 220, which changes the output of the detector 220, such as voltage.

The infrared light source 212 may be set to emit a specific infrared light wavelength spectrum depending on the target gas. It may be understood that each gas expelled will absorb infrared wavelengths differently. For example, carbon dioxide absorbs infrared waves with wavelengths of about 4.25 micrometers, while oxygen does not absorb at all.

In addition to the foregoing components, sensor module 204 may further comprise a micro-processor 230, a non-transitory computer-readable storage medium 240 (e.g. memory) and a communication element 250, which may all be incorporated on printed circuit board (PCB) 167.

Infrared detector 220 may be electrically and operationally connected, particularly via printed circuit board (PCB) 167, to micro-processor 230 and non-transitory computer-readable storage medium 240 to record operational data, which may be stored on medical device 10, and more particularly hub connection fitting 70.

The operation data may also be communicated to at least one remote electronic device 900, which may be part of a computer communication network, at near real time with communication element 250. In the event the operational data is communicated to the computer(s) of the communication network, such may also be stored in a non-transitory computer-readable storage medium of the computer(s) of the communication network, or communicated and stored on another computer(s) of another communication network. At least one remote electronic device may comprise a computer such as a desktop computer, a portable computer such as a laptop computer, a notebook computer, a netbook (with or without a keyboard such as an iPad), a personal digital assistant (PDA), or a wearable computer, a cellphone computer or other handheld computer (e.g. smartphone).

The communication element 250 may transmit electronic communication to, and receive electronic communication from, the computer(s) of the communication network using wireless communication standards and protocols (e.g. WiFi, Bluetooth, cellular). As such, it should be understood that the communication element 250 of medical device 10 may particularly be either a one-way communication element (e.g. transmitter) or a two-way communication element (e.g. transmitter and/or receiver, such as a transceiver) for allowing the medical device 10, and more particularly hub connection fitting 70, to communicate with the computer(s) of computer network. Thus, medical device 10, and more particularly hub connection fitting 70 may contain all the computer (software) application programs and electronic circuitry to enable communication therebetween, such as signals which may include data (e.g. raw, interpreted, binary). In addition to one or more computer processors, such circuitry may include digital and analog integrated circuits, resistors, capacitors, transistors and other semiconductors and other electronic components known to those skilled in the art.

In the foregoing manner, medical device 10, and more particularly hub connection fitting 70 may transmit data (e.g. voltage signals representative of carbon dioxide presence) via the transmitter to the computer(s) of the communication network. The computer(s) of the computer network, and more particularly (micro) processor(s) of the computer(s) may then convert the data/signals to an output (e.g. graph and/or numerical display) representative of expiratory carbon dioxide using hardware and/or software including an algorithm, which may be shown on a computer output display. A display may be understood as a computer output surface and projecting mechanism that shows text and often graphic images to the computer user, using a cathode ray tube (CRT), liquid crystal display (LCD), light-emitting diode (LED), gas plasma (GS), or other image projection technology. The display may be a touch activated screen.

Alternatively, the processor 250 of the hub connection fitting 70, and more particularly the sensor module 204, may convert the data/signals to an output (e.g. graph and/or numerical display) representative of expiratory carbon dioxide using hardware and/or software including an algorithm. The output graph and/or numerical display of expiratory carbon dioxide may then be transmitted to the computer(s) of the communication network for display on a computer display of the computer(s) of the communication network, or displayed on the medical device.

In other embodiments, medical device, and more particularly sensor module 204, may include its own output display 260 which may be a numeric display of expiratory carbon dioxide. The output display 260 may be an LED display, which may be similar in size to that of a digital watch.

As an alternative to a graphical or numeric display, output display 260 of medical device, and more particularly sensor module 204, may include a plurality of output lights which correspond to different levels of measured carbon dioxide, such as a red LED, a yellow LED and a green LED. For example, a lighted red LED would be indicative of no measured carbon dioxide, a lighted yellow LED would be indicative of a low level of measured carbon dioxide and a lighted green LED would be indicative of a suitable level of measured carbon dioxide. Alternatively, a single lighted LED would be indicative of no measured carbon dioxide, two lighted LEDs would be indicative of a low level of measured carbon dioxide and three lighted LEDs would be indicative of a suitable level of measured carbon dioxide. The LEDs may be the same or different colors. Similarly, the light output from LED 165 may also change colors when the sensor apparatus 200 is in use. For example, when sensor apparatus 200 is not in use, LED 165 may emit white (colorless) light. However, when sensor apparatus 200 is in use, light from LED 165 may go from white light to various colors of the electromagmetic spectrum. For example, red light (wavelength between 610 nm and 750 nm) may be indicative of no measured carbon dioxide, yellow light (wavelength between 570 nm and 590 nm) may be indicative of a low level of measured carbon dioxide and green light (wavelength between 495 nm and 570 nm) may be indicative of a suitable level of measured carbon dioxide.

It also may be beneficial for LED 165 to only emit red light, such as for medical personnel treating soldiers in the field. As opposed to white light, the red light emitted by LED 165 may be less detectable by an enemy combatant.

In the foregoing manner, medical device 10, and more particularly hub connection fitting 70 may also receive communication from one or more computers of a computer network. Such may be used to calibrate the sensor 202 prior to use with a known concentration of the target gas.

In other embodiments, sensor 202 when comprising a carbon dioxide sensor, may use technologies other than capnography to detect and measure carbon dioxide. For example sensor 202 may be a chemical carbon dioxide sensor, or an electro-chemical carbon dioxide sensor as known in the art. Sensor 202 may also be a raman spectroscopy sensor, such as a surface-enhanced raman spectroscopy sensor, a photoacoustic sensor (e.g. for photoacoustic spectroscopy) or a mass spectrometry sensor.

Figure 18:
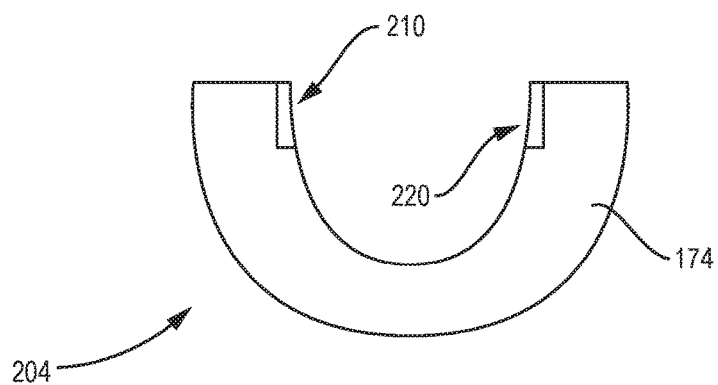
FIG. 18 is a top view of a sensor module according to another embodiment of the endotracheal tube apparatus.
Figure 19:
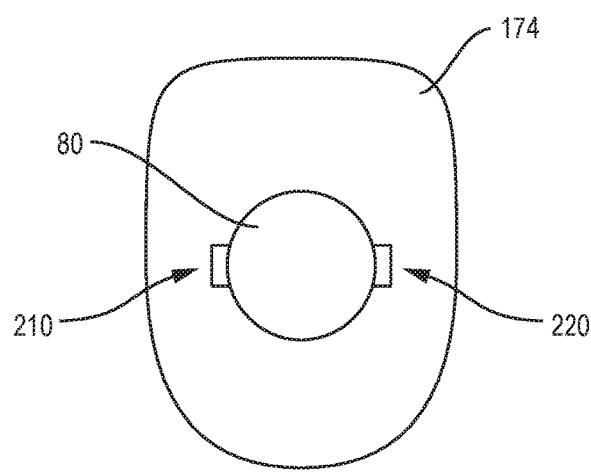
FIG. 19 is top view of a sensor module according to another embodiment of the endotracheal tube apparatus.

In other embodiments, as shown in FIG. 18, a single sensor module 204 may include both the infrared emitted 210 and the infrared detector 220 arranged in a housing 174, which is semi-circular. In FIG. 19, the housing may be annular and define a portion of ventilation passageway 80.

In other embodiments, sensor apparatus 200, and more particular sensor 202, may comprise a temperature sensor, such as a thermistor/thermocouple, particularly to measure temperature of inhaled and exhaled respiratory gas(es) of the patient. In other embodiments, a temperature sensor and method of use as disclosed in U.S. Pat. No. 8,323,207 to Popov et al., hereby incorporated by reference, may be used to measure temperature of inhaled and exhaled respiratory gas(es) of the patient.

In still other embodiments, the tubular light guide 178 may be part of the sensor 202, and more particularly a temperature sensor, in which case the temperature sensor may comprise a fiber optical thermometer, which may make use of a gallium arsenide (GaAs) semiconductor crystal that is mounted on the end of the tubular light guide 178. In such instance, second light guide 178 may be used for the fiber optical thermometer in addition to a first light guide 178 to emit light (see FIG. 13B).

In still other embodiments, alternatively or in addition to, sensor apparatus 200 may include sensors 202 to detect and/or quantify other gas(es) within the composition of respiration gas exhaled by a patient other than carbon dioxide, such as oxygen, nitrogen, and carbon monoxide (to detect carbon monoxide poisoning), using known sensor technologies which may be incorporated into tube apparatus 20, such as hub connection fitting 70.

As may be understood from the foregoing embodiments, the tube apparatus 20, such as an endotracheal apparatus, may also incorporate a sensor apparatus 200 to detect one or more physiological parameters applicable to the health state of a host to reduce or eliminate reliance on additional equipment to perform such detection.

As also set forth above, tube apparatus 20, and more particularly an endotracheal tube apparatus, may reduce stack-up of multiple components and associated air leaks occurring there between by combining multiple features into a hub connection fitting 70 of the endotracheal tube apparatus 20.

For example, a conventional medical device stack-up to perform pulmonary ventilation on a patient in cardiac arrest may first involves intubation with a endotracheal tube, which includes a standard connection piece at the working end. Once intubated by medical personnel, a separate diverging capnography adaptor may then be connected to the standard connection piece of the endotracheal tube as dictated by standard of care. Attachment of the diverging capnography adaptor is required to confirm proper placement of the endotracheal tube, continuously monitor for carbon dioxide output and identify a return to spontaneous circulation. Thereafter, an impedance threshold device (ITD) may be connected to the top of the diverging capnography adaptor and a bag valve mask (BVM) is connected to the top of the impedance threshold device (ITD). Alternatively, the order of capnography adaptor and impedance threshold (ITD) may be reversed in the foregoing stack-up.

A medical device 10 comprising a tube 30 and a hub connection fitting 70 as disclosed herein may comprise other airway management devices, such as a supraglottic airway laryngopharyngeal tube (SALT) apparatus, which comprises an supraglottic airway laryngopharyngeal tube and a hub connection fitting.

A medical device 10 comprising a tube 30 and a hub connection fitting 70 as disclosed herein may be used in pulmonary applications involving inspection, diagnosis and/or treatment where one or more devices are passed through each passageway to perform procedures in the lungs, such as lung resection or biopsy sample (tissue) extraction.

A medical device 10 comprising a tube 30 and a hub connection fitting 70 as disclosed herein may be used in gastrointestinal applications involving inspection, diagnosis and/or treatment where one or more devices are passed through each passageway to perform procedures in the gastrointestinal tract. Such procedures may involve the esophagus, stomach, intestines such as the duodenum, and the colon. Specific procedures may include gastric bypass or other stomach reduction.

A medical device 10 comprising a tube 30 and a hub connection fitting 70 as disclosed herein may be used in cardiology for the insertion of pacing leads or other diagnostic electrical leads.

For minimally invasive surgery, multiple surgical related devices can be inserted through the tube 30 and a hub connection fitting 70 to the procedure site, which each device using a separate lumen of the tube 30 and a hub connection fitting 70 to improve control, safety and/or efficacy of the surgical devices.

In the foregoing applications, it should be understood that the tube 30 and a hub connection fitting 70 may both have appropriately sized passageways for such applications, which may be larger or smaller than the passageways required for use as an endotracheal tube apparatus. As such, the tube 30 and a hub connection fitting 70 may be provided in kits with multiple quantities, sizes and angle of the passageways through the hub connection fitting 70. The number of passageways is only limited by the outside dimensions of the tube and required internal dimensions of the passageways.

Referring now to FIGS. 20A-25B, there is shown another embodiment of a medical device 10 comprising a tube apparatus 20, and more particularly an endotracheal tube apparatus 20 of a medical (respiratory) system 2 (see FIG. 1) according to the present disclosure. As with prior embodiments, while a remainder of the disclosure may refer to the tube apparatus as being an endotracheal tube apparatus 20, it should be understood that the present disclosure is not limited to an endotracheal tube apparatus 20, and the present tube apparatus may have other medical applications, as well as non-medical applications, other than that of endotracheal tube apparatus 20.

As shown in FIGS. 20A-20D, as with prior embodiments, the endotracheal tube apparatus 20 comprises a flexible, elongated, hollow endotracheal tube 30 and a hub connection fitting 70. For simplicity, only a proximal region of the endotracheal tube 30 is shown, however, it may be understood that the distal region of the endotracheal tube 30 may be the same as the distal region of the endotracheal tube 30 shown in FIG. 8. Additional views of the hub connection fitting 70 and endotracheal tube prior to assembly are shown in FIGS. 21A-21I and FIGS. 22A-22B, respectively.

Figure 20C:
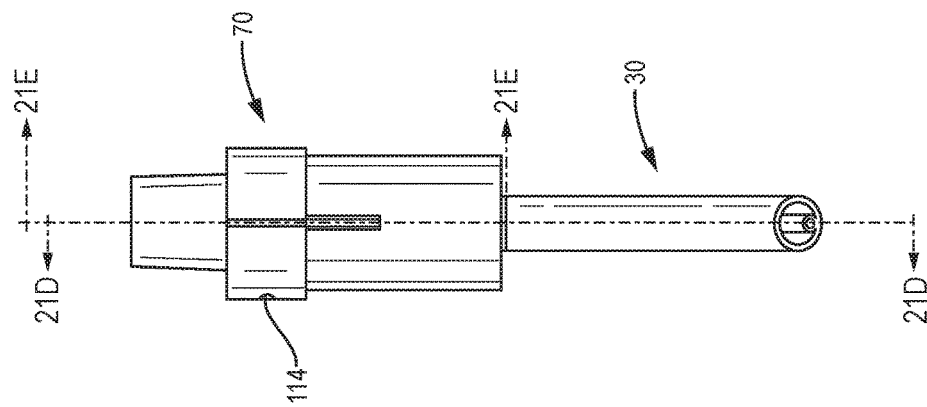
FIG. 20C is a second side view of the endotracheal tube apparatus of FIG. 20A.
Figure 20B:
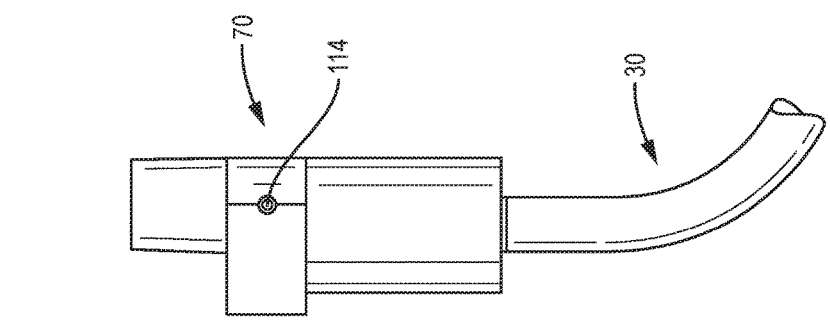
FIG. 20B is a first side view of the endotracheal tube apparatus of FIG. 20A.
Figure 20A:
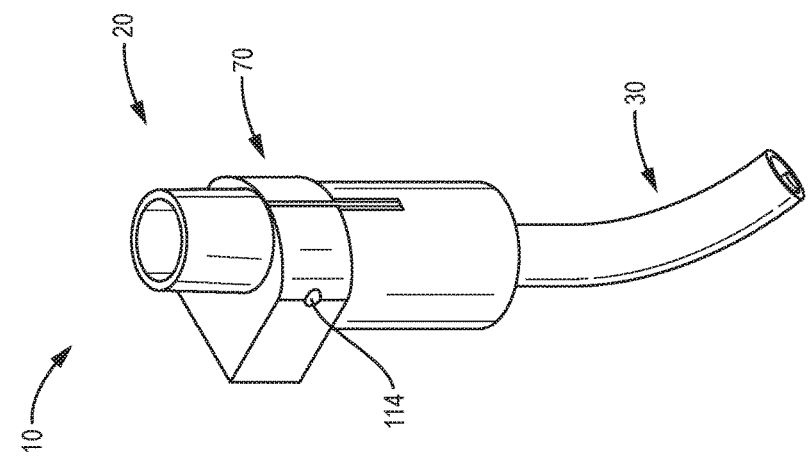
FIG. 20A is a perspective view of another embodiment of the endotracheal tube apparatus.
Figure 20D:
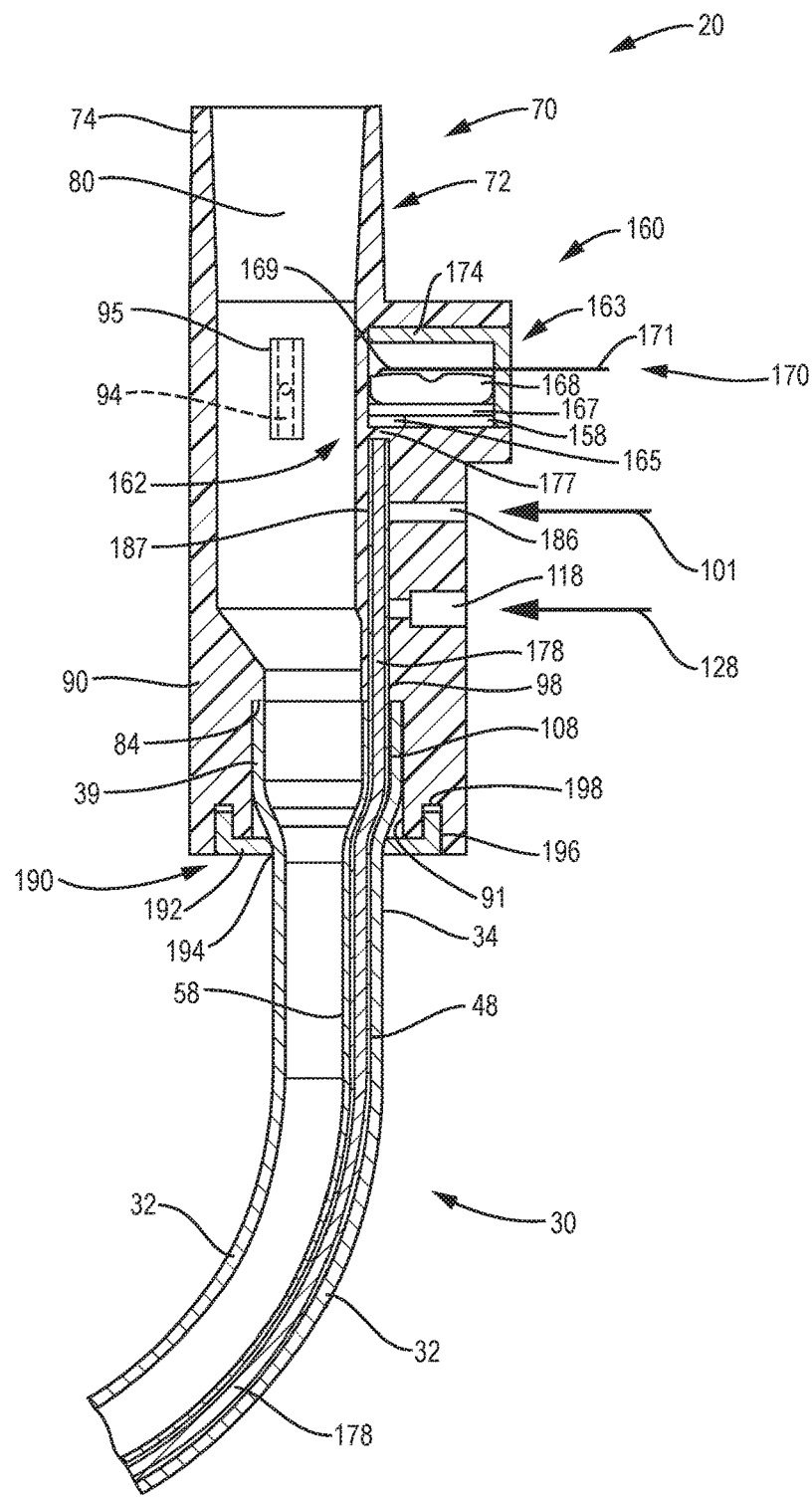
FIG. 20D is a longitudinal cross sectional side view of the endotracheal tube apparatus of FIG. 20A taken along line 20D-20D of FIG. 20C.
Figure 21A:
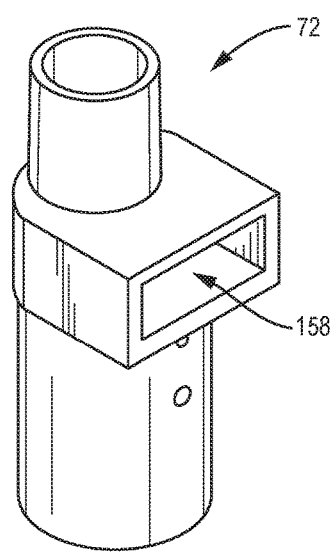
FIG. 21A is a top perspective view of a hub connection fitting of the endotracheal tube apparatus of FIG. 20A.
Figure 21B:
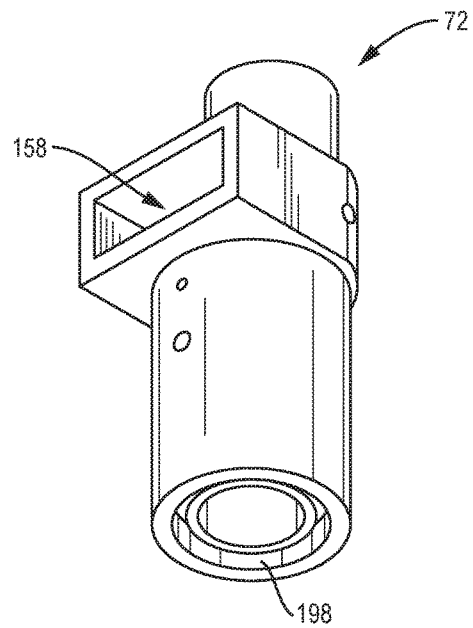
FIG. 21B is a bottom perspective view of the hub connection fitting of FIG. 20A.
Figure 21C:
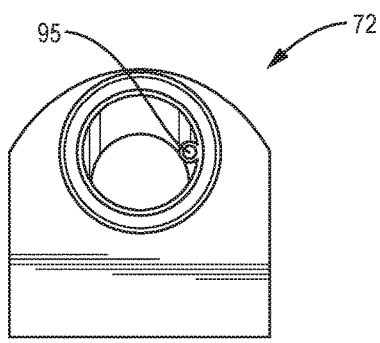
FIG. 21C is a top view of the hub connection fitting of FIG. 20A.
Figure 21D:
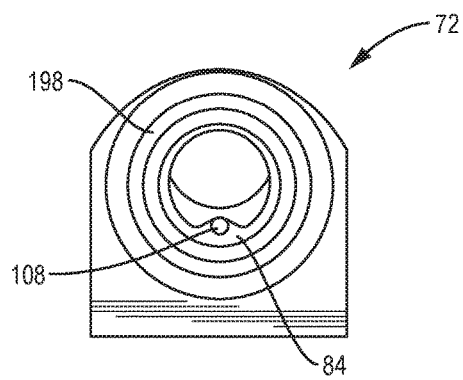
FIG. 21D is a bottom view of the hub connection fitting of FIG. 20A.
Figure 21E:
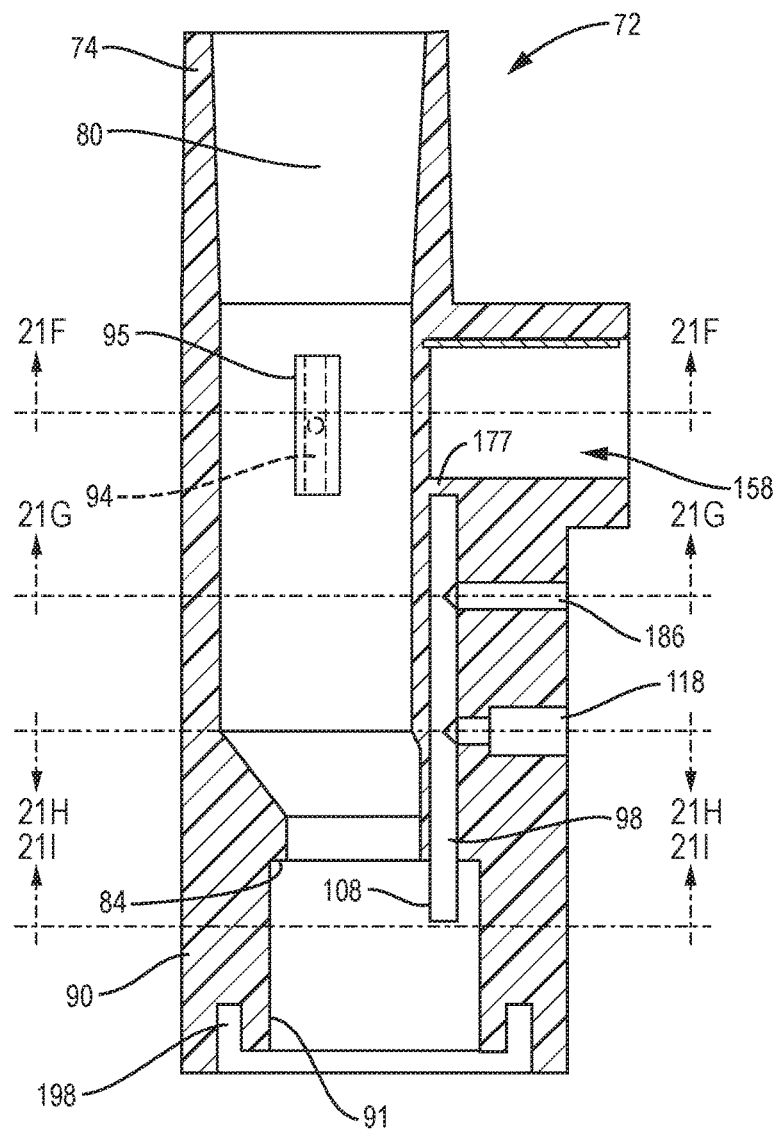
FIG. 21E is a longitudinal cross sectional side view of the hub connection fitting of FIG. 20A taken along line 21E-21E of FIG. 20C.

Referring now to FIG. 20D, similar to at least one prior embodiment, endotracheal tube apparatus 20 may include a lighting apparatus 160. Lighting apparatus 160 may comprise a light-emitting device 162, which may include a light-source module 163 coupled with hub connection fitting body 72. Similar to FIG. 9, light-source module 163 may be insertable into and removable from a light-source module receptacle 158 formed in the hub connection fitting body 72.

With particular reference to FIG. 20D, light-source module 163 may comprise one or more light sources 165, particularly in the form of a lamp such as one or more light-emitting diodes (LEDs). The LED 165 may be arranged as part of a light engine, which may comprise an LED driver including a printed circuit board (PCB) 167 to which the LED 165 is mounted as well as the electrical wiring/circuitry to control and provide power/signals to the LED 165.

Similar to FIG. 10, and as shown in FIG. 20D, light-source module 163 may further comprise a housing 174, which forms a cavity 175 to receive the printed circuit board (PCB) 167, as well as power source (battery) 168, battery holder 169 and removable non-conductive liner 170 which extends through aperture 171. Similar to FIG. 10, LED 165 and battery holder 169 each provide conductive terminals to electrically couple LED 165 and battery 168, respectively, to printed circuit board 167 to establish an electrical circuit there between. Additional views of the light source module 163 are shown in FIGS. 23A-23D and FIGS. 24A-24B. As shown in FIG. 24B, the inner surfaces of the housing 174 may be made reflective, such as with a reflective coating 161, to inhibit light from LED 165 from projecting upwards from the hub connection fitting 70.

As shown in FIG. 20D, similar to at least one prior embodiment, when endotracheal tube apparatus 20 is provided by the manufacturer, the battery 168 may be out of electrical communication with LED 165 to inhibit the LED 165 from powering prior to desired use. In such regard, a removable non-conductive liner 170 with a pull tab 172 may be initially positioned between the electrical conductor 166 and the battery 168 to temporarily disconnect the electrical circuit.

Thereafter, when endotracheal tube apparatus 20 is to be used, the removable non-conductive liner 170 may be removed from hub connection fitting 70 by simply pulling on pull tab 172 with a pulling force, which may remove the removable non-conductive liner 170 from hub connection fitting 70 the establish electrical contact between battery 168 and electrical conductor 166 to provide power to printed circuit board 167 and LED 165. As such, it should be understood that lighting apparatus 160, and more particularly light-source module 163, makes use of a switchless design with no "on-off switch." More particularly, the lighting apparatus 160 is configured for single use and will continue to operate until power from the battery 168 will no longer provide power to light the LED 165. However, it should be understood that lighting apparatus 160 may also make use of an on-off switch as such switches are known in the art.

Once the light-source module 163 is assembled similar to FIG. 9, it may be assembled to hub connection fitting body 72 by being inserted into light-source module receptacle 158 formed in the hub connection fitting body 72 by sliding light-source module 163 into light-source module receptacle 158.

In certain embodiments, after a single use of light-source module 163 and the associated power drain of battery 168 upon removal of removable non-conductive liner 170, it may be possible to detachably remove light-source module 163 from hub connection fitting body 72 by sliding the light-source module 163 out of light-source module receptacle 158. Thereafter, battery 168 and removable non-conductive liner 170 may be replaced with a new replacement (charged) battery 168 and a new removable non-conductive liner 170 for reuse of light-source module 163.

In other embodiments, it may be desirable to inhibit removal of light-source module 163 from hub connection fitting body 72 to deter reuse of hub connection fitting 70. In such regard, light-source module 163 and hub connection fitting body 72 may be adhesively bonded to each other, particularly by applying an adhesive (e.g. cyanoacrylate, epoxy) to an exterior surface of the housing 174 to be in contact with the hub connection fitting body 72 prior to inserting the light-source module 163 into light-source module receptacle 158. Thereafter, before the adhesive sets (e.g. cures and/or cools), the light-source module 163 may be slid into light-source module receptacle 158 after which time the adhesive may set. Alternatively, or in addition to the use of a separate adhesive, once the light-source module 163 is slid into light-source module receptacle 158, the housing 174 and the hub connection fitting body 72 may be welded together, such as by vibration welding or ultrasonic welding in a known manner, for a more permanent assembly.

Similar to the embodiment of FIGS. 8-13, LED 165 is arranged to direct light down the longitudinal length of the endotracheal tube 30 along the longitudinal axis, while the thickness of the printed circuit board 167 and the battery 168 are arranged transverse to the longitudinal axis. Also similar to the embodiment of FIGS. 8-13, in order to provide increased light emittance at the distal end of tube apparatus 20, lighting apparatus 160, and more particularly, light-emitting device 162 may further comprise a tubular light guide 178 which extends along the length of endotracheal tube 30.

As shown, light from LED 165 is transmitted through a wall 177 of the light-source module receptacle 158 of hub connection fitting body 72 which is beneath the LED 165, with the proximal end 179 of the tubular light guide 178 adjacent and aligned with the LED 165 such that the LED 165 overlies the proximal end 179 of the tubular light guide 178.

In such embodiment, the hub connection fitting body 72, and more particularly wall 177, is light transmissive to visible light (e.g. substantially transparent). In such regards, the hub connection fitting 72 may be made of polycarbonate or polymethylmethacrylate (acrylic).

As a result of light from LED 165 passing through wall 177 before entering tubular light guide 178, in contrast to the embodiment of FIGS. 8-13, the hub connection fitting body 72 does not need to include an aperture 159 located at inner end of the light-source module receptacle 158, and the LED 165 and the portion of the printed circuit board 167 to which LED 165 is mounted do not enter into ventilation passageway 80 of hub connection fitting body 72.

Tubular light guide 178 may be formed of a bendable, light transmissive (e.g. substantially transparent) cylinder of extruded thermoplastic polymer (e.g. polycarbonate) or glass. Tubular light guide 178 may comprise a fiber optic cable having a single elongated optical fiber or a plurality of elongated optical fibers (i.e. a multi-fiber fiber optic cable). Tubular light guide 178 may be a solid cylinder, which may contain and transmit light by total internal reflection, or a hollow cylinder which may contain and transmit light along a reflective lining. As shown, tubular light guide 178 is a solid, cylindrical elongated optical fiber, particularly formed of glass, which may have a diameter in a range of 0.1 mm to 2 mm (including all ranges and increments there between) and more particularly in a range of 0.4 mm to 1.1 mm (including all ranges and increments there between).

Tubular light guide 178 may be located within one of secondary passageways 44, 46 or 48 to emit light at or adjacent the distal end opening 42 of endotracheal tube 30. As shown, tubular light guide 178 is arranged in secondary passageway 98 of hub connection fitting which is in fluid communication with secondary passageway 48 of endotracheal tube 30.

As set forth herein, secondary passageways 98 and 48 define a portion of the cuff inflation passageway in fluid communication with cuff inflation port 28 and inflation cuff 49. In the foregoing manner, air pressure to inflate inflation cuff 49 and light to illuminate the distal end of the endotracheal tube 30 may be extended through a single secondary passageway of hub connection fitting body 72 and endotracheal tube 30 to reduce the overall number of secondary passageways. While the passageway for the drug delivery port 26 is not shown, such has been eliminated from the drawing to reduce complexity.

Similar to the embodiment of FIGS. 8-13, with regards to assembly, the distal end of secondary passageway 98 is defined by a male connector portion 108 of the hub connection fitting body 72 which is dimensioned to be inserted into secondary passageway 48 of endotracheal tube 30 and interference (frictionally) fit with the inside diameter of the side wall 58, while the proximal end of the endotracheal tube 30 is to contact and butt against annular lip 84 of distal body portion 76.

Further, annular ring 90, which was initially separate from the hub connection fitting body 72 is now provided as one piece with the hub connection fitting body 72 and form a recess/cavity 92 into which a proximal end (cylindrical) region 39 of the endotracheal tube 30 may be inserted and overlap against, particularly with the outer surface 34 of the proximal end (cylindrical) region 39 of the endotracheal tube 30 in contact with the inner (cylindrical) surface 91 of the recess 92. It should be understood that any combination of interference fits, adhesive bonding and welding may be used to mechanically (positive mechanical and/or friction) and/or adhesively join the proximal end (cylindrical) region 39 of the endotracheal tube 30 within recess 92, particularly with the outer surface 34 of the proximal end (cylindrical) region 39 of the endotracheal tube 30 in contact with the inner (cylindrical) surface 91 of the recess 92. For example, the outer surface 34 of the proximal end (cylindrical) region 39 of the endotracheal tube 30 may be at least one of interference fit, adhesive bonded and welded with the inner (cylindrical) surface 91 of the recess 92. It should be understood that any combination of interference fits, adhesive bonding and welding may be used for any of the connections alone or in conjunction with another joining method.

Tubular light guide 178 may be inserted into secondary passageway 98 of hub connection fitting body 72 and secondary passageway 48 of endotracheal tube 30 before or after the hub connection fitting body 72 and endotracheal tube 30 are assembled. As shown, tubular light guide 178 may have an outer diameter which is less than or substantially equal (i.e. within manufacturing tolerance) to the inner diameter of secondary passageway 98.

In a particular method of assembly, the tubular light guide 178 may first be inserted into secondary passageway 48 of endotracheal tube 30 until the distal end 180 of the tubular light guide 178 makes contact with plug 182 already inserted therein. A remaining proximal end portion of the tubular light guide 178 not contained within the secondary passageway 48 of endotracheal tube 30 may then be inserted into the secondary passageway 98 of hub connection fitting body 72 until male connector portion 108 is inserted in secondary passageway 48 of endotracheal tube 30. Tubular light guide 178 may then be retained in the secondary passageway 98, 48 between the wall 177 of hub connection fitting body 72 and plug 182 of endotracheal tube 30.

Unlike the embodiment of FIGS. 8-13, wall 177 of the hub connection fitting closes the proximal end of secondary passageway 98. As a result, no sealing composition 101 is required to seal a proximal end of the secondary passageway 98 against air leaks (in the case where air pressure to inflate inflation cuff 49 and light to light the distal end of the endotracheal tube 30 extend through the same secondary passageway 98, 48 of hub connection fitting body 72 and endotracheal tube 30), the gap 181 between the LED 165 and the proximal end of secondary passageway 98 and tubular light guide 178.

In the event is it desirable to adhesively bond the tubular light guide 178 to the side wall 99 of secondary passageway 98, particularly to fix one end of the tubular light guide 178 to hub connection fitting body 72, the sealing composition 101 may be introduced through injection port 186. As with the embodiment of FIGS. 8-13, the polymer may be located between the inside diameter of secondary passageway 98 and the outside diameter of the tubular light guide 178 adjacent the distal end thereof (above/proximal to counter-bore 118) to adhesively bond the tubular light guide 178 to the side wall 99 of secondary passageway 98. In addition to or as an alternative to sealing composition 101, a cylindrical (annular) bushing 187 may be used to retain the tubular light guide 178 to hub connection fitting body 72.

While not shown, as with the embodiment of FIGS. 8-13, secondary passageway 48 of endotracheal tube 30 may be sealed distal to air inlet/outlet opening 50 (see FIG. 8) with a plug 182 of light transmissive (e.g. substantially transparent) polymer material.

As with the embodiment of FIGS. 8-13, it may be desirable for the tubular light guide 178 to be shorter than the overall length of the secondary passageway 98, 48 such that the tubular light guide 178 may slide freely therein. Similarly, the tubular light guide may slide in secondary passageways 98, 48 in a range of 0.5 mm to 6 mm (including all ranges and increments there between) and more particularly in a range of 1 mm to 4 mm) including all ranges and increments there between).

In such case, the tubular light guide 178 may not be bonded to the side wall 99 or 58 of either secondary passageway 98 or 48, respectively, but be retained in the secondary passageway 98, 48 between wall 177 of hub connection fitting body 72 and the plug 182 at the distal end of the secondary passageway 48. As a result, the tubular light guide 178 may be less opt to break when endotracheal tube 30 undergoes bending. In the event it becomes desirable to bond the tubular light guide 178 to the side wall 99 and/or 58 of either secondary passageway 98 or 48, respectively, the tubular light guide 178 should not be bonded at more than one fixed point, again to inhibit the likelihood of breaking when endotracheal tube 30 undergoes bending.

In order to reduce the diameter of secondary passageway 48 potentially to the smallest diameter to accommodate tubular light guide 178, a proximal end region 43 of a length of the secondary passageway 48 is flared such that it has a greater inner diameter than the remaining distal region of the length of secondary passageway 48. In such a manner, the larger diameter of the proximal end region 43 of the secondary passageway 48 as compared to the more distal region of the length of secondary passageway 48 may better accommodate the insertion of male connector portion 108 therein.

Similar to the embodiment of FIGS. 8-13, counter-bore 118 is configured to receive the distal end portion of tubing segment 128 in fluid communication with the cuff inflation port 28, which comprises a cuff inflation port connector 148, which connects with a cuff inflation device 800.

Similar to the embodiment of FIGS. 8-13, the present embodiment also includes a counter-bore 114 to receive the distal end portion of tubing segment 124 in fluid communication with the fluid sampling port 24, which may comprise a filter 142 and fluid sampling port threaded connector 144, which connects fluid sampling port to an analyzing/monitoring apparatus 600. Also similar to the embodiment of FIGS. 8-13, the secondary passageway 94 defined by side wall 95 has been shortened to eliminate male connector portion 104, particularly as the corresponding secondary passageway 44 in endotracheal tube 30 has been eliminated.

Figure 22B:
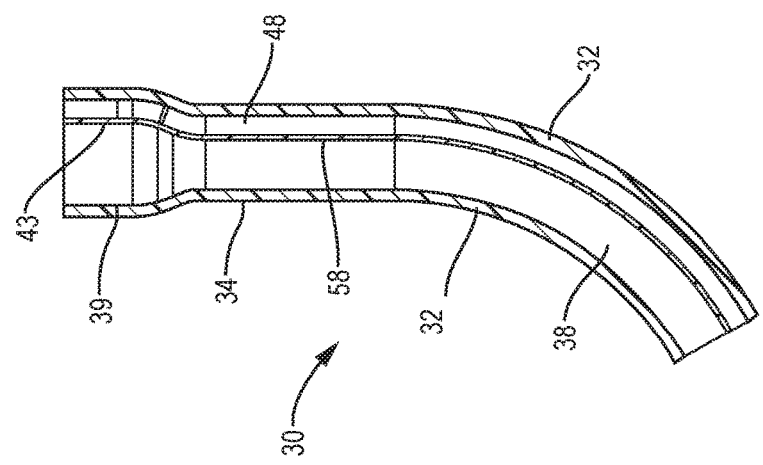
FIG. 22B is a longitudinal cross-sectional side view of the endotracheal tube of FIG. 22A taken along line 22B-22B of FIG. 22A.
Figure 22A:
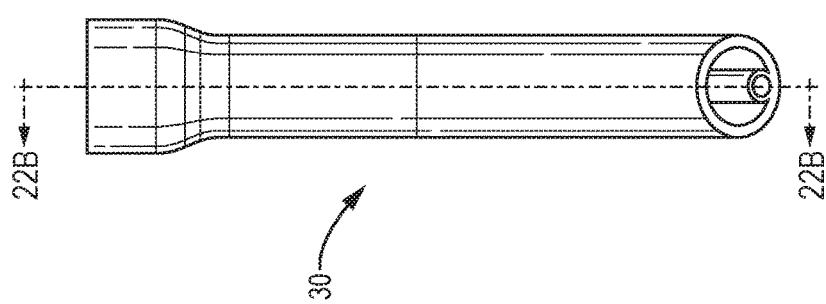
FIG. 22A is a side view of an endotracheal tube of the endotracheal tube apparatus of FIG. 20A.

As best shown in FIGS. 22A-22B, proximal end (cylindrical) region 39 of a length of the endotracheal tube 30 may be flared such that it has a greater outer diameter than the remaining distal region of the length of the endotracheal tube 30. In such a manner, the outer diameter of the distal region of the length of the endotracheal tube 30 may change in accordance with different sized endotracheal tubes 30 (to accommodate patients of different sizes such as pediatric, adolescent, adult) while the outer diameter of the proximal end (cylindrical) region 39 of the endotracheal tubes 30 may remain constant as to attach to a universally sized hub connection fitting 70.

In addition to the foregoing, an endotracheal tube connector 190, which is also shown in FIGS. 25A-25B, may be used to mechanically connect the endotracheal tube 30 to the hub connection fitting body 72. As shown endotracheal tube connector 190 comprises an annular disc 192 defining an aperture 194 and having a peripheral lip 196. Peripheral lip 196 is configured to mate with an interference fit within a circular recess 198 formed in the distal end of hub connection fitting body 72.

As shown the diameter of aperture 194 is smaller than the outer diameter of the proximal (cylindrical) end region 39 of the endotracheal tube 30 which is flared. As such, in the event the outer surface 34 of the proximal end (cylindrical) region 39 of the endotracheal tube 30 is not adequately connected to inner (cylindrical) surface 91 of the recess 92, the annular disc 192 will inhibit the endotracheal tube 30 from separating from the hub connection fitting body 72.

In certain embodiments, the endotracheal tube connector 190 may be color coded to the size of the endotracheal tubes 30. In other words, a first color (e.g. blue) of the endotracheal tube connector 190 may be matched to a first size (e.g. small) of the endotracheal tube 30; a second color (e.g. red) of the endotracheal tube connector 190 may be matched to a second size (e.g. medium) of the endotracheal tube 30; a third color (e.g. green) of the endotracheal tube connector 190 may be matched to a third size (e.g. large) of the endotracheal tube 30; etc. In the foregoing manner, a clinician or other medical treatment personnel may be quickly made aware of the size of the endotracheal tube apparatus 30 so as to determine if the size is suitable for the patient.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS 2 medical system
10 medical device
20 tube apparatus
24 fluid sampling port (carbon dioxide sampling port)
26 drug delivery port
28 cuff inflation port
30 tube
31 proximal end of tube
32 outer cylindrical side wall
32a outer cylindrical side wall
32b outer cylindrical side wall
33 distal end of tube
34 outer surface of tube
36 inner surface of tube
38 ventilation passageway of tube
39 proximal end region of tube
40 proximal end opening of tube
41 common longitudinal (center) axis of tube
42 distal end opening of tube
43 proximal (flared) end region of secondary passageway
44 secondary passageway (fluid sampling passageway)
46 secondary passageway (drug delivery passageway)
48 secondary passageway (cuff inflation passageway)
49 inflation cuff
50 inflation cuff opening
54 semi cylindrical side wall
56 semi cylindrical side wall
58 semi cylindrical side wall
70 hub connection fitting
72 hub connection fitting body
74 proximal body portion
76 distal body portion
78 intermediate/middle body portion
80 ventilation passageway
82 annular lip/shoulder
84 annular lip/shoulder
86 annular lip/shoulder
90 annular ring
91 inner (cylindrical) surface
92 recess
94 secondary passageway
95 side wall
96 secondary passageway
97 side wall
98 secondary passageway
99 side wall
100 notch
101 sealing composition
104 male connector portion
106 male connector portion
108 male connector portion
114 counter-bore
116 counter-bore
118 counter-bore
124 tubing segment
126 tubing segment
128 tubing segment
134 passageway (lumen)
136 passageway (lumen)
138 passageway (lumen)
142 filter
143 colorimetric paper
144 fluid sampling port threaded connector
146 drug delivery port connector
148 cuff inflation port connector
158 light-source module receptacle
159 aperture
160 lighting apparatus
161 reflective surface
162 light-emitting device
163 light-source module
164 lighting device
165 lamp/light source
166 electrical conductor
167 printed circuit board
168 power source (battery)
169 battery holder
170 non-conductive liner
171 elongated aperture
172 pull tab of non-conductive liner
173 elbow
174 housing
175 housing cavity
176 light reflective surface
177 wall of hub connection fitting body 178 tubular light guide
179 proximal end of tubular light guide
180 distal end of tubular light guide
181 gap
182 plug
183 plug body
184 plug body recess
185 through-hole
186 injection port
187 bushing
190 endotracheal tube connector
192 annular disc
194 aperture
196 peripheral lip
198 circular recess
200 sensor apparatus
202 sensor
204 sensor module
206 sensor module receptacle
210 infrared emitter
212 infrared light source
218 interference filter
220 infrared detector
230 processor
240 non-transitory computer-readable storage medium
250 communication element
260 sensor output display
500 respirator apparatus (bag valve mask)
502 respirator tube passageway
504 respirator tube
506 respirator tube side wall
600 analyzing/monitoring apparatus
650 syringe
700 drug delivery device
800 cuff inflation device
900 remote electronic device

What is claimed is:

1. An endotracheal tube apparatus having a proximal end and a distal end, and further comprising:
   an endotracheal tube having a proximal end and a distal end;
   a hub connection fitting connected to the endotracheal tube, the hub connection fitting disposed adjacent the proximal end of the endotracheal tube proximal to the proximal end of the endotracheal tube;
   the endotracheal tube configured to be inserted into a trachea of a human body;
   a ventilation passageway disposed in the hub connection fitting and along a length of the endotracheal tube;
   a cuff inflation passageway disposed in the hub connection fitting and the endotracheal tube;
   a light emitting device comprising a light source and a tubular light guide, the light source and the tubular light guide arranged such that light, when emitted from the light source, is transmitted along a longitudinal axis of the tubular light guide;
   the light source disposed in the hub connection fitting; and
   the tubular light guide disposed in the endotracheal tube within the cuff inflation passageway.

2. The endotracheal tube apparatus of claim 1 wherein:
   the hub connection fitting comprises a hub connection fitting body;
   the light emitting device comprises a light-source module; and
   the light source module is contained in the hub connection fitting body.

3. The endotracheal tube apparatus of claim 2 wherein:
   the light source module comprises at least one light-emitting diode mounted to a printed circuit board, and a battery.

4. The endotracheal tube apparatus of claim 3 wherein:
   the light source module comprises a housing which contains the battery, and the printed circuit board; and
   the housing is contained in the hub connection fitting body.

5. The endotracheal tube apparatus of claim 1, wherein:
   the hub connection fitting has a proximal connector portion and a distal connector portion.

6. The endotracheal tube apparatus of claim 5, wherein:
   the proximal connector portion and the distal connector portion are provided by a single body.

7. The endotracheal tube apparatus of claim 5, wherein:
   the proximal connector portion is configured to be connected to a respirator tube.

8. The endotracheal tube apparatus of claim 5, wherein:
   the proximal connector portion is a male connector portion.

9. The endotracheal tube apparatus of claim 5, wherein:
   the proximal connector portion is cylindrical.

10. The endotracheal tube apparatus of claim 5, wherein:
    the distal connector portion is connected to the endotracheal tube.

11. The endotracheal tube apparatus of claim 1, further comprising:
    a cuff inflation port in fluid communication with the cuff inflation passageway.

12. The endotracheal tube apparatus of claim 1, further comprising:
    the cuff inflation passageway extends through the hub connection fitting.

13. The endotracheal tube apparatus of claim 1, wherein:
    a cuff inflation port in fluid communication with the cuff inflation passageway, the cuff inflation port joined to the hub connection fitting by a tubing segment.

14. The endotracheal tube apparatus of claim 1, wherein:
    the tubular light guide is fixed in position relative to the hub connection fitting by a composition.

15. The endotracheal tube apparatus of claim 14, wherein:
    the composition comprises at least one of a polymer, adhesive or potting resin.

16. The endotracheal tube apparatus of claim 1, wherein:
    a distal end of the cuff inflation passageway is sealed with a plug.

17. The endotracheal tube apparatus of claim 16, wherein:
    the plug is light transmissive.

18. The endotracheal tube apparatus of claim 16, wherein:
    the tubular light guide terminates in the cuff inflation passageway prior to the plug.

19. The endotracheal tube apparatus of claim 16, wherein:
    the tubular light guide terminates within the plug.

20. The endotracheal tube apparatus of claim 16, wherein:
    the tubular light guide extends through the plug.

21. The endotracheal tube apparatus of claim 1, wherein:
    the tubular light guide comprises at least one optical fiber.

22. The endotracheal tube apparatus of claim 1, wherein:
    the tubular light guide has a diameter in a range of 0.1 mm to 2 mm.

23. The endotracheal tube apparatus of claim 1, wherein:
    the tubular light guide is formed of at least of a polymer or glass.

24. The endotracheal tube apparatus of claim 1, wherein:
the tubular light guide as a proximal end; and
the proximal end of the tubular light guide is disposed in the hub connection fitting.

25. The endotracheal tube apparatus of claim 1, wherein:
the tubular light guide as a distal end; and
the distal end of the tubular light guide is disposed in the endotracheal tube.

26. The endotracheal tube apparatus of claim 1, wherein:
the light source is disposed proximally adjacent a proximal end of the tubular light guide.

27. The endotracheal tube apparatus of claim 1, further comprising:
an inflation cuff arranged to be inflatable by transmitting a fluid through the cuff inflation passageway; and
the inflation cuff joined to the endotracheal tube.

* * * * *